US012420224B2

(12) United States Patent
Jones et al.

(10) Patent No.: US 12,420,224 B2
(45) Date of Patent: Sep. 23, 2025

(54) PORTABLE APPARATUS AND SYSTEM FOR INDOOR AIRBORNE PATHOGEN CONTROL

(71) Applicant: Jones Deal LLC, Summerville, SC (US)

(72) Inventors: Timothy J. Jones, Summerville, SC (US); Jeffery Lee Deal, Charleston, SC (US)

(73) Assignee: Jones Deal LLC, Summerville, SC (US)

( * ) Notice: Subject to any disclaimer, the term of this patent is extended or adjusted under 35 U.S.C. 154(b) by 915 days.

(21) Appl. No.: 17/515,262

(22) Filed: Oct. 29, 2021

(65) Prior Publication Data

US 2022/0410050 A1     Dec. 29, 2022

Related U.S. Application Data

(63) Continuation-in-part of application No. 17/357,971, filed on Jun. 24, 2021, now Pat. No. 11,253,805.
(Continued)

(51) Int. Cl.
*B01D 46/00*  (2022.01)
*A61L 9/20*   (2006.01)
*B01D 46/44*  (2006.01)

(52) U.S. Cl.
CPC ............ *B01D 46/0028* (2013.01); *A61L 9/20* (2013.01); *B01D 46/0049* (2013.01);
(Continued)

(58) Field of Classification Search
None
See application file for complete search history.

(56) References Cited

U.S. PATENT DOCUMENTS

| | | | |
|---|---|---|---|
| 1,136,784 A | | 4/1915 | Fair |
| 1,939,312 A | * | 12/1933 | Murray .................. E06B 7/082 |
| | | | 454/274 |

(Continued)

FOREIGN PATENT DOCUMENTS

| | | | |
|---|---|---|---|
| CA | 2740742 A1 | * | 11/2011 |
| CN | 105034756 A | * | 11/2015 |

(Continued)

OTHER PUBLICATIONS

International search report and Written Opinion of the International Searching Authority, International application No. PCT/US22/34969. Date of mailing: Nov. 17, 2022. ISA/US, Alexandria, VA.

*Primary Examiner* — Brit E. Anbacht
(74) *Attorney, Agent, or Firm* — Gregory Finch; Finch Paolino, LLC

(57) ABSTRACT

A portable airborne pathogen control apparatus and system. Aspects of the present disclosure provide for a portable airborne pathogen control apparatus configured to be selectively positioned within an interior room and configured to enable a floor-to-ceiling flow of air within the interior room. The portable airborne pathogen control apparatus may comprise a housing with an air intake disposed at a lower area of a base housing and an air outlet disposed at an upper area of an elongated duct extending from the base housing. A blower fan housed within an interior chamber of the housing may be configured to direct a floor-to-ceiling flow of air through the interior chamber from the air intake to the air outlet. A volume of air directed through the interior chamber of the housing may be disinfected using one or more UV-C emitters and/or cold plasma generator(s) housing in the interior chamber of the housing.

18 Claims, 14 Drawing Sheets

Related U.S. Application Data

(60) Provisional application No. 63/230,033, filed on Aug. 5, 2021.

(52) U.S. Cl.
CPC ....... B01D 46/442 (2013.01); *A61L 2209/111* (2013.01); *A61L 2209/14* (2013.01); *B01D 2273/30* (2013.01); *B01D 2279/51* (2013.01); *B01D 2279/65* (2013.01)

(56) References Cited

U.S. PATENT DOCUMENTS

| | | | | |
|---|---|---|---|---|
| 2,308,262 | A * | 1/1943 | Beil | F24F 13/18 454/195 |
| 2,579,099 | A * | 12/1951 | Sherry | E06B 7/02 49/374 |
| 4,295,417 | A * | 10/1981 | Isley | E06B 7/02 49/63 |
| 5,120,273 | A * | 6/1992 | Lin | F24F 13/18 454/212 |
| 5,387,775 | A * | 2/1995 | Kang | F23G 7/06 110/244 |
| 5,481,829 | A * | 1/1996 | Waytashek | E06B 7/086 49/82.1 |
| 5,738,706 | A * | 4/1998 | Swanander | B01D 46/446 55/467 |
| 5,894,130 | A * | 4/1999 | Bach | A61L 2/10 250/436 |
| 6,093,229 | A * | 7/2000 | Lee | B01D 46/0086 55/385.2 |
| 6,099,607 | A * | 8/2000 | Haslebacher | F24F 3/163 55/482 |
| 6,152,996 | A * | 11/2000 | Linnersten | B01D 53/0415 55/497 |
| 6,451,252 | B1 * | 9/2002 | Ruan | A61L 9/16 422/186.04 |
| 6,455,014 | B1 * | 9/2002 | Hammerstrom | H05H 1/2465 422/186.04 |
| 7,568,659 | B2 * | 8/2009 | Roques | B64D 45/0028 49/31 |
| 7,824,480 | B2 | 11/2010 | Hurlebaus et al. | |
| 9,370,600 | B1 * | 6/2016 | DuPuis | F21V 14/08 |
| 10,012,408 | B1 * | 7/2018 | Crittenden | E06B 7/04 |
| 10,337,238 | B1 * | 7/2019 | Crittenden | E06B 7/082 |
| 10,918,993 | B1 * | 2/2021 | Saha | B01D 53/85 |
| 2002/0193064 | A1 * | 12/2002 | Michalakos | F24F 11/63 454/257 |
| 2003/0137794 | A1 * | 7/2003 | Izumi | A61L 9/22 361/231 |
| 2006/0057020 | A1 | 3/2006 | Tufo | |
| 2006/0130492 | A1 * | 6/2006 | Park | A47J 36/2433 62/77 |
| 2008/0086994 | A1 * | 4/2008 | Descotes | F24F 1/005 55/471 |
| 2009/0042502 | A1 * | 2/2009 | Kim | B60H 3/0078 361/231 |
| 2009/0051263 | A1 * | 2/2009 | Hayashi | A61L 9/20 313/485 |
| 2011/0126828 | A1 * | 6/2011 | Wu | B03C 3/155 128/205.12 |
| 2011/0272595 | A1 * | 11/2011 | Neister | A61L 9/22 250/435 |
| 2013/0092029 | A1 * | 4/2013 | Morgan | E03F 5/08 96/111 |
| 2014/0260994 | A1 * | 9/2014 | Grider | B01D 46/44 55/467 |
| 2016/0250370 | A1 * | 9/2016 | Orito | A61L 9/014 422/122 |
| 2017/0016638 | A1 | 1/2017 | Yun | |
| 2019/0143301 | A1 * | 5/2019 | Huang | D06M 11/59 8/115.54 |
| 2019/0231919 | A1 * | 8/2019 | Mehnert | A61L 9/127 |
| 2019/0234136 | A1 * | 8/2019 | Lu | E06B 7/092 |
| 2020/0179544 | A1 * | 6/2020 | Ufkes | A61L 2/10 |
| 2020/0206375 | A1 * | 7/2020 | Ufkes | A61L 9/20 |
| 2021/0322589 | A1 * | 10/2021 | Matter | A61L 2/26 |
| 2021/0322594 | A1 * | 10/2021 | Ahmad | A61L 2/10 |
| 2023/0039310 | A1 | 2/2023 | Baarman et al. | |
| 2023/0270908 | A1 | 8/2023 | Lehmann | |
| 2024/0390534 | A1 * | 11/2024 | Wang | A61L 2/24 |

FOREIGN PATENT DOCUMENTS

| | | |
|---|---|---|
| CN | 107780794 A * | 3/2018 |
| CN | 111321991 A | 6/2020 |
| DE | 202009017541 U1 * | 10/2010 |
| WO | WO-2007116130 A1 * | 10/2007 |

\* cited by examiner

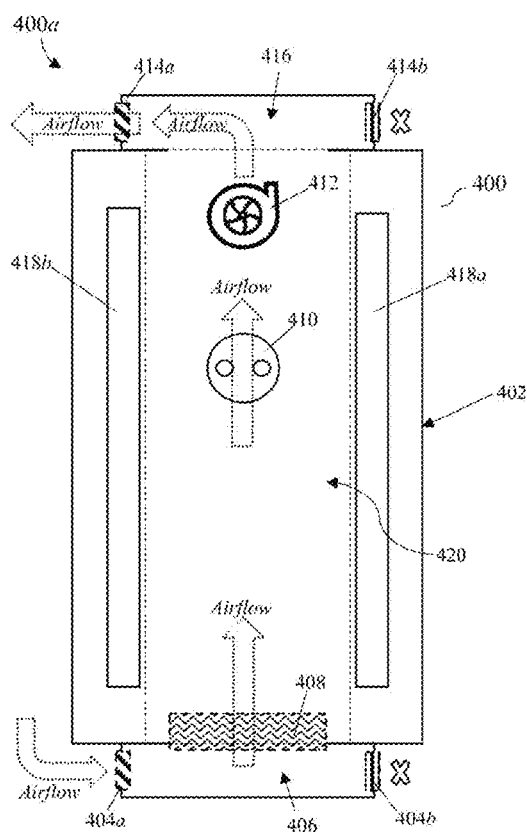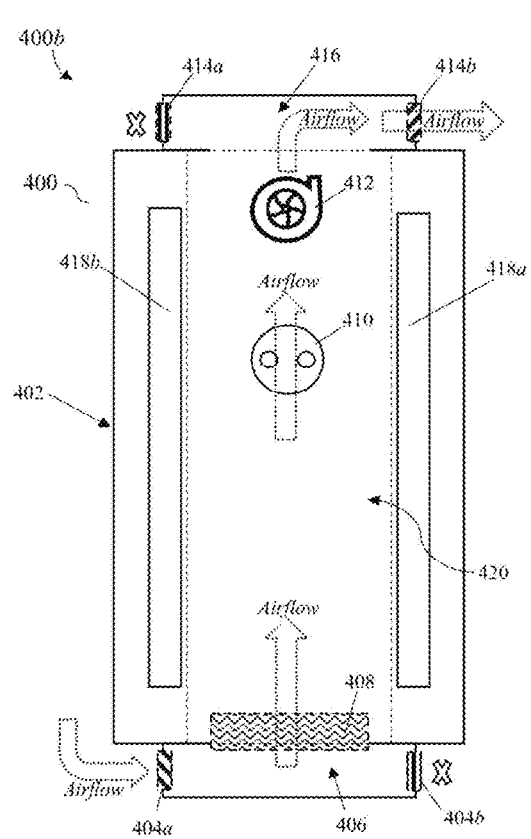
FIG. 4A
FIG. 4B

PORTABLE APPARATUS AND SYSTEM FOR INDOOR AIRBORNE PATHOGEN CONTROL

CROSS REFERENCE TO RELATED APPLICATIONS

The present patent application is a continuation-in-part of U.S. patent application Ser. No. 17/357,971 filed on Jun. 24, 2021, entitled "APPARATUS AND SYSTEM FOR INDOOR AIRBORNE PATHOGEN CONTROL" and also claims the benefit of U.S. provisional application Ser. No. 63/230,033, filed on Aug. 5, 2021; each of these applications being hereby incorporated in their entireties, at least by virtue of this reference.

FIELD

The present disclosure relates to the field of infection control systems; in particular, a portable apparatus and system for airborne pathogen control within an interior area of a dwelling.

BACKGROUND

Respiratory infections can be acquired from exposure to pathogens contained either in droplets or droplet nuclei. Exposure to microorganisms in droplets (e.g., through aerosolized oral and nasal secretions from infected patients) constitutes a form of direct contact transmission. When droplets are produced during a sneeze or cough, a cloud of infectious particles >5 μm in size is expelled, resulting in the potential exposure of susceptible persons within 3 feet of the source person. Examples of pathogens spread in this manner are influenza virus, rhinoviruses, adenoviruses, and respiratory syncytial virus (RSV). The spread of airborne infectious diseases via droplet nuclei is a form of indirect transmission. Droplet nuclei are the residuals of droplets that, when suspended in air, subsequently dry and produce particles ranging in size from 1-5 μm. These particles can contain potentially viable microorganisms, be protected by a coat of dry secretions, remain suspended indefinitely in air, and be transported over long distances.

The microorganisms in droplet nuclei persist in favorable conditions (e.g., a dry, cool atmosphere with little or no direct exposure to sunlight or other sources of radiation). Pathogenic microorganisms that can be spread via droplet nuclei include, for example, *Mycobacterium tuberculosis*, VZV, measles virus (i.e., rubeola), and smallpox virus (i.e., variola major). Several environmental pathogens have life-cycle forms that are similar in size to droplet nuclei and may exhibit similar behavior in the air. The spores of *Aspergillus fumigatus* have a diameter of 2-3.5 μm, with a settling velocity estimated at 0.03 cm/second (or about 1 meter/hour) in still air. With this enhanced buoyancy, the spores, which resist desiccation, can remain airborne indefinitely in air currents and travel far from their source.

Buildings have been associated with spread of infectious diseases, such as outbreaks of measles, influenza, and *Legionella*. With SARS-CoV-2 (also known as COVID-19), most outbreaks involving three or more people have been linked to time spent indoors, and evidence confirms that far-field airborne transmission (defined as within-room but beyond 6 feet) of SARS-CoV-2 is occurring. Controlling concentrations of indoor respiratory aerosols to reduce airborne transmission of infectious agents is critical. Current solutions to control the spread of infectious diseases in interior environments include source control strategies (e.g., masking, physical distancing) and engineering controls (e.g., ventilation and filtration systems and apparatuses). In addition, outbreaks of diseases such as SARS-CoV-2 present unique treatment challenges for hospitals and healthcare facilities where limited rooms are available for appropriate isolation of patients infected with highly contagious pathogens. What is needed, therefore, is a solution to enable hospitals to convert a normal patient room quickly and efficiently into an isolation or reverse isolation room to accommodate unexpected or fluctuating patient load on an as-needed basis.

Through applied effort, ingenuity, and innovation, Applicant has identified several deficiencies and problems with airborne pathogen control in interior environments. Applicant has developed a solution that is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Certain aspects of the present disclosure provide for a portable airborne pathogen control apparatus comprising a base housing comprising a plurality of wheels coupled to a bottom surface of the base housing; an air intake vent disposed on a surface of the base housing; a HEPA filter disposed in an interior portion of the base housing; an air chamber extending from an upper surface of the base housing; at least one UV-C emitter disposed in an interior portion of the air chamber, wherein the at least one UV-C emitter is configured to pulse an emission of UV radiation to the interior portion of the air chamber; a cold plasma generator coupled to a portion of the air chamber; an air output vent disposed on an upper portion of the air chamber; and a blower fan coupled to a portion of the air chamber, wherein the blower fan is configured to establish an airflow path from the air intake vent through the HEPA filter and through the air chamber to the air output vent.

In accordance with certain aspects of the present disclosure, a surface of the HEPA filter may comprise at least one antimicrobial agent disposed thereon, wherein the at least one antimicrobial agent is selected from the group consisting of monoterpene phenol, thymol and carvacrol. In certain embodiments, the air chamber may be constructed from a flexible or bendable material. In certain embodiments, the at least one UV-C emitter is configured to pulse the emission of UV radiation at a wavelength in the range of 200 nm to 280 nm. In certain embodiments, the at least one UV-C emitter is configured to pulse a dual band emission of UV radiation at a first wavelength in the range of 200 nm to 280 nm and a second wavelength in the range of 200 nm to 280 nm, wherein the first wavelength is different from the second wavelength. In accordance with certain aspects of the present disclosure, the portable airborne pathogen control apparatus may further comprise a particulate counter comprising at least one optical sensor configured to measure a gross number of particulate present in a volume of air passing through the air output vent. In accordance with certain aspects of the present disclosure, the portable airborne pathogen control apparatus may further comprise one or more pre-filter disposed on an upstream surface of the HEPA filter. In accordance with certain aspects of the present disclosure, the portable airborne pathogen control apparatus may further comprise a counterweight disposed on the bottom surface of the base housing.

Further aspects of the present disclosure provide for a portable airborne pathogen control apparatus comprising a portable housing comprising a bottom, side walls and a top defining an exterior surface and an internal chamber defining an airflow path from an air intake aperture disposed on a lower area of the housing to an air outlet aperture disposed on an upper area of the housing; at least one air filter housed in the internal chamber of the housing; a blower fan housed in the internal chamber of the housing and operably configured to establish a flow of air through the internal chamber from the air intake aperture to the air outlet aperture; at least one UV-C emitter housed in the internal chamber of the housing, wherein the at least one UV-C emitter is configured to pulse an emission of UV radiation at a wavelength in the range of 200 nm to 280 nm to the interior portion of the air chamber; and a cold plasma generator housed in the internal chamber of the housing.

In accordance with certain aspects of the present disclosure, the portable airborne pathogen control apparatus may be configured wherein the at least one UV-C emitter is configured to pulse a dual band emission of UV radiation at a first wavelength in the range of 200 nm to 280 nm and a second wavelength in the range of 200 nm to 280 nm, wherein the first wavelength is different from the second wavelength. In accordance with certain aspects of the present disclosure, the portable airborne pathogen control apparatus may be configured wherein the housing is configured to be removably coupled to a surface of a wall of an interior room. In accordance with certain aspects of the present disclosure, the portable airborne pathogen control apparatus may be configured wherein a surface of the air filter comprises at least one antimicrobial agent disposed thereon, wherein the at least one antimicrobial agent is selected from the group consisting of monoterpene phenol, thymol and carvacrol. In accordance with certain aspects of the present disclosure, the portable airborne pathogen control apparatus may be configured wherein the at least one UV-C emitter is coupled to an interior surface of the top of the portable housing adjacent to the air outlet aperture. In accordance with certain aspects of the present disclosure, the portable airborne pathogen control apparatus may further comprise a first flexible duct coupled to the air intake aperture. In accordance with certain aspects of the present disclosure, the portable airborne pathogen control apparatus may further comprise a second flexible duct coupled to the air outlet aperture. In accordance with certain aspects of the present disclosure, the portable airborne pathogen control apparatus may further comprise a particulate counter housed in the internal chamber of the housing and comprising at least one optical sensor configured to measure a gross number of particulate present in a volume of air passing through the air outlet aperture.

Still further aspects of the present disclosure provide for a portable airborne pathogen control apparatus comprising a base housing comprising a bottom, side walls and a top defining an exterior surface and an internal chamber and at least one air inlet aperture on at least one side of the base housing; a rigid elongated duct extending from an opening of the top of the base housing at a proximal end of the rigid elongated duct and comprising at least one air inlet aperture at a distal end of the rigid elongated duct, wherein the internal chamber of the base housing and an interior area of the rigid elongated duct comprise an airflow path for the portable airborne pathogen control apparatus; at least one air filter disposed in the internal chamber of the base housing; a blower fan configured to establish a flow of air through the airflow path from the at least one air inlet aperture to the at least one air outlet aperture; at least one UV-C emitter housed in the interior area of the rigid elongated duct; and a cold plasma generator housed in the interior area of the rigid elongated duct. In accordance with certain aspects of the present disclosure, the portable airborne pathogen control apparatus may be configured wherein the at least one UV-C emitter is configured to pulse the emission of UV radiation at a wavelength in the range of 200 nm to 280 nm. In accordance with certain aspects of the present disclosure, the portable airborne pathogen control apparatus may further comprise a particulate counter housed in the interior area of the rigid elongated duct and comprising at least one optical sensor configured to measure a gross number of particulate present in a volume of air passing through the at least one air outlet aperture. In accordance with certain aspects of the present disclosure, the portable airborne pathogen control apparatus may be configured wherein the blower fan, the base housing and the rigid elongated duct are configured to establish a floor to ceiling flow of air in an interior room of a building.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 4A and 4B are functional diagrams of an indoor airborne pathogen control apparatus, in accordance with certain aspects of the present disclosure;

DETAILED DESCRIPTION

Figure 1:
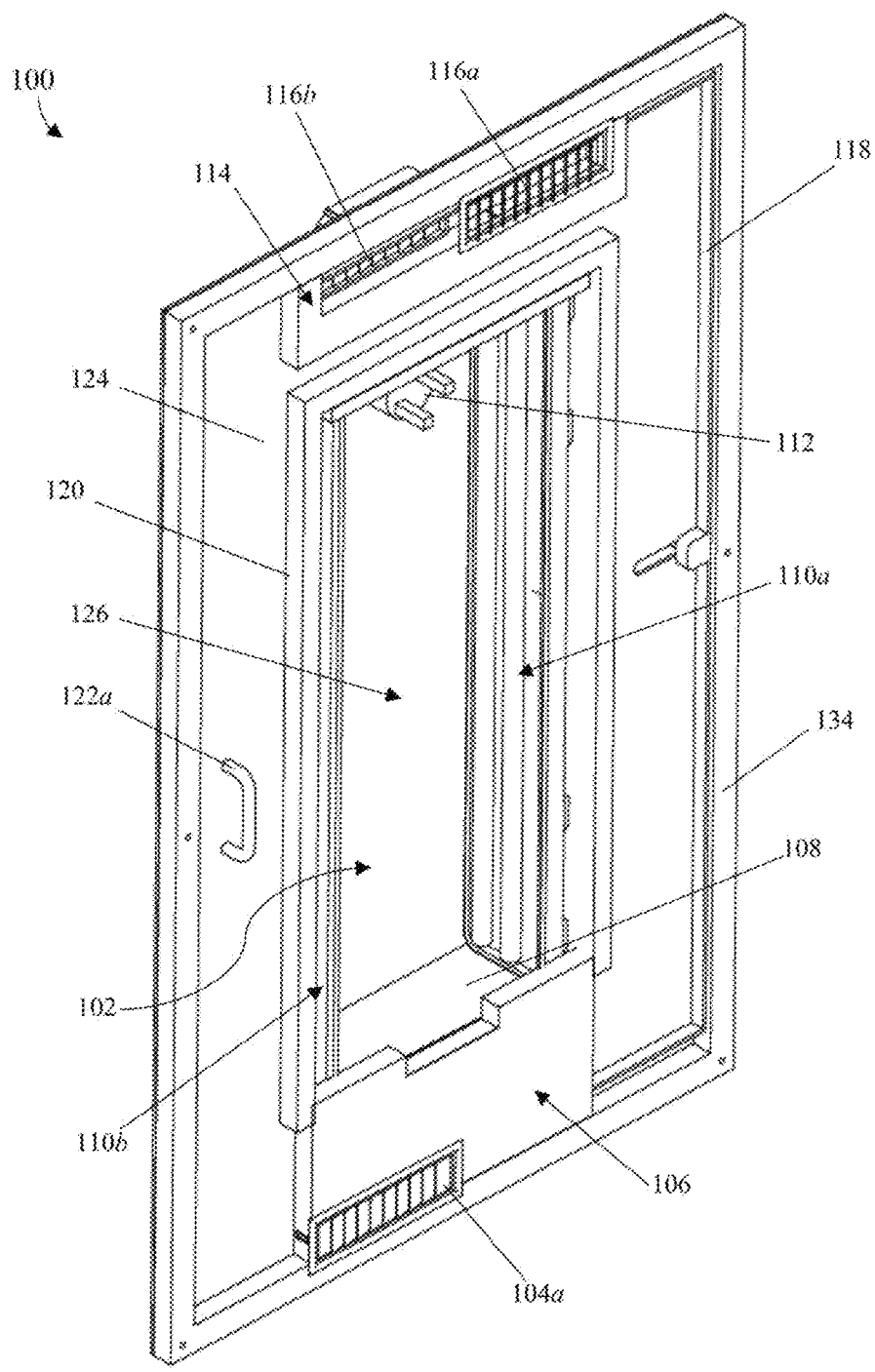
FIG. 1 is a front perspective view of an indoor airborne pathogen control apparatus, in accordance with certain aspects of the present disclosure.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout. All definitions, as defined and used herein, should be understood to control over dictionary definitions, definitions in documents incorporated by reference, and/or ordinary meanings of the defined terms.

Following below are more detailed descriptions of various concepts related to, and embodiments of, inventive methods, devices and systems configured to provide for an environmental control and air treatment system configured to control a flow of air and modify an atmospheric pressure of an interior room of a building. Certain embodiments of the present disclosure provide for a door-mounted control unit configured to decontaminate/sanitize a volume of air drawn into an interior chamber of the unit comprising one or more infection control modalities before being expelled from a directional output duct/vent. The door-mounted control unit may comprise a controller communicably engaged with one or more sensors, mobile electronic device and/or remote server configured to configure, modify and/or regulate one or more operational modes/settings of the door-mounted control unit.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, and the term "including" means including but not limited to. The term "based on" means based at least in part on.

As used herein, the term "interface" refers to any shared boundary across which two or more separate components of a computer system may exchange information. The exchange can be between software, computer hardware, peripheral devices, humans, and combinations thereof. The term "interface" may be further defined as any shared boundary or connection between two dissimilar objects, devices or systems through which information or power is passed and/or a mechanical, functional and/or operational relationship is established and/or accomplished. Such shared boundary or connection may be physical, electrical, logical and/or combinations thereof. An exemplary system, method, and apparatus according to the principles herein may include a door-mounted control unit with one or more directional intake vents at the floor level and one or more directional outlet vents at the door head level configured to draw air into and out of the apparatus using an internal blower fan. Air is passed across a true HEPA filter, which may be impregnated with a monoterpene phenol, thymol and/or carvacrol. The filtered air is then passed across a dielectric barrier generating cold plasma. As the filtered air moves through the device, it passes through a light field of UV-C light before being discharged at the one or more directional outlet vents. In accordance with certain embodiments, the door housing unit comprises an array of UV-C and/or near-UV emitters disposed on a surface of the door frame and configured to generate an emission of UV-C and/or near-UV light at the door frame upon opening/closing the door.

In accordance with an exemplary use case provided by embodiments of the present disclosure, a volume of contaminated air is drawn into an interior chamber of a door housing unit, passed through an air filtration device, passed across a cold plasma generator and through an emission of UV-C radiation. A directional airflow of decontaminated air is directed into or out of a contamination area to minimize potential exposure to respiratory contagions.

Certain benefits and advantages of the present disclosure include a multimodal airborne pathogen control apparatus and system configured to direct and decontaminate a volume of indoor air of occupied spaces and reduce the risk of spreading airborne contagions. Certain aspects of the multimodal airborne pathogen control apparatus and system may include one or more infection control modalities including, but not limited to, dielectric Cold Plasma generation, non-ozone producing UV-C light, True HEPA filtration comprising a monoterpene phenol-impregnated filter material, and configurable intake/output ducting to direct airflow to/from a desired area and regulate interior atmospheric pressure.

Further benefits and advantages of the present disclosure include an airborne pathogen control apparatus and system configured to control/direct a flow of air from an interior room of a building to reduce the spread of airborne pathogens.

Further benefits and advantages of the present disclosure include an air treatment apparatus and system configured to control/regulate the atmospheric pressure of an interior room of a building in a healthcare setting.

Further benefits and advantages of the present disclosure include an indoor environmental control apparatus and system configured to enable hospitals and other patient treatment facilities to convert a normal patient room quickly and efficiently into an isolation or reverse isolation room to accommodate unexpected or fluctuating patient load on an as-needed basis.

An exemplary system, method, and apparatus according to the principles herein may include a portable airborne pathogen control apparatus that sequesters and inactivates airborne microorganisms via one or more germicidal control methodologies including, but not limited to, HEPA filtration, cold plasma generation, and germicidal ultraviolet light in the UV-C spectrum (e.g., 254 nm) to decontaminate air in occupied spaces and a floor-to-ceiling air current. In accordance with certain aspects of the present disclosure, an air intake at the floor level (where airborne contagions tend to be concentrated) is filtered through a 3 µm HEPA filter. The air is then passed through a cold plasma generator and then flows past high-intensity germicidal UV light. The floor-to-ceiling airflow enhances the effectiveness of providing clean air nearer the respiratory zone for occupants of an indoor environment while helping to direct a downward flow of aerosolized contagions, decreasing the likelihood of inhalation of contaminated air.

An exemplary system, method, and apparatus according to the principles herein may include a portable airborne pathogen control apparatus comprising a weighted unit on wheels configured to be moved from location to location (e.g., room to room) within an indoor environment (e.g., a building). In accordance with certain aspects of the present disclosure, a portable airborne pathogen control apparatus may comprise a housing configured to be mounted to a wall of an interior room and comprise an air intake adjacent to a floor of the interior room and an air outlet adjacent to a ceiling of the interior room to enable a floor-to-ceiling airflow within the interior room. In accordance with certain aspects of the present disclosure, the housing of the portable airborne pathogen control apparatus may have a profile depth in the range of about 3 inches to about 12 inches when mounted to the wall of the interior room.

An exemplary system, method, and apparatus according to the principles herein may include a portable airborne pathogen control apparatus comprising an "I-shaped" design comprising a baseboard intake vent and a ceiling outflow vent containing a germicidal UV-C light bar in the ceiling outflow vent. In accordance with certain aspects of the present disclosure, the portable airborne pathogen control apparatus may comprise a flexible intake and/or outflow vent configured to direct a flow of air into and/or out of an interior room to create a negative pressure or positive pressure environment within the interior room.

An exemplary system, method, and apparatus according to the principles herein may include a portable airborne pathogen control apparatus configured to be removably coupled to a hospital bed and comprising an intake vent at the foot of the bed or under the bed and an output vent at the head of the bed.

Certain benefits and advantages of the present disclosure include a portable airborne pathogen control apparatus operably configured to reduce the spread of airborne contagions (e.g., nosocomial infections like pneumonia, influenza, COVID 19 and *C. difficile* colitis) among staff and patients in health care settings.

Certain benefits and advantages of the present disclosure include a portable airborne pathogen control apparatus operably configured to reduce the spread of airborne contagions among students and teachers in educational settings.

Certain benefits and advantages of the present disclosure include a portable airborne pathogen control apparatus operably configured to reduce the spread of airborne contagions to protect vulnerable individuals from airborne contagions in shared interior spaces and clinical areas.

Certain benefits and advantages of the present disclosure include: (a) reduced energy usage in clean room environments due to eliminating the need to re-condition air as required by traditional negative pressure systems; (b) reduced overuse of antibiotics and potential for increased bacterial resistance within healthcare settings; (c) improved environmental benefits including stable temperature and humidity; (d) elimination of systemic negative pressures throughout a building, thereby reducing potential invitation of molds and other pathogens from dark spaces in the building; and (e) preserved human dignity in healthcare settings by less perceived isolation barrier, as compared to traditional negative pressure or clean room systems.

Figure 2:
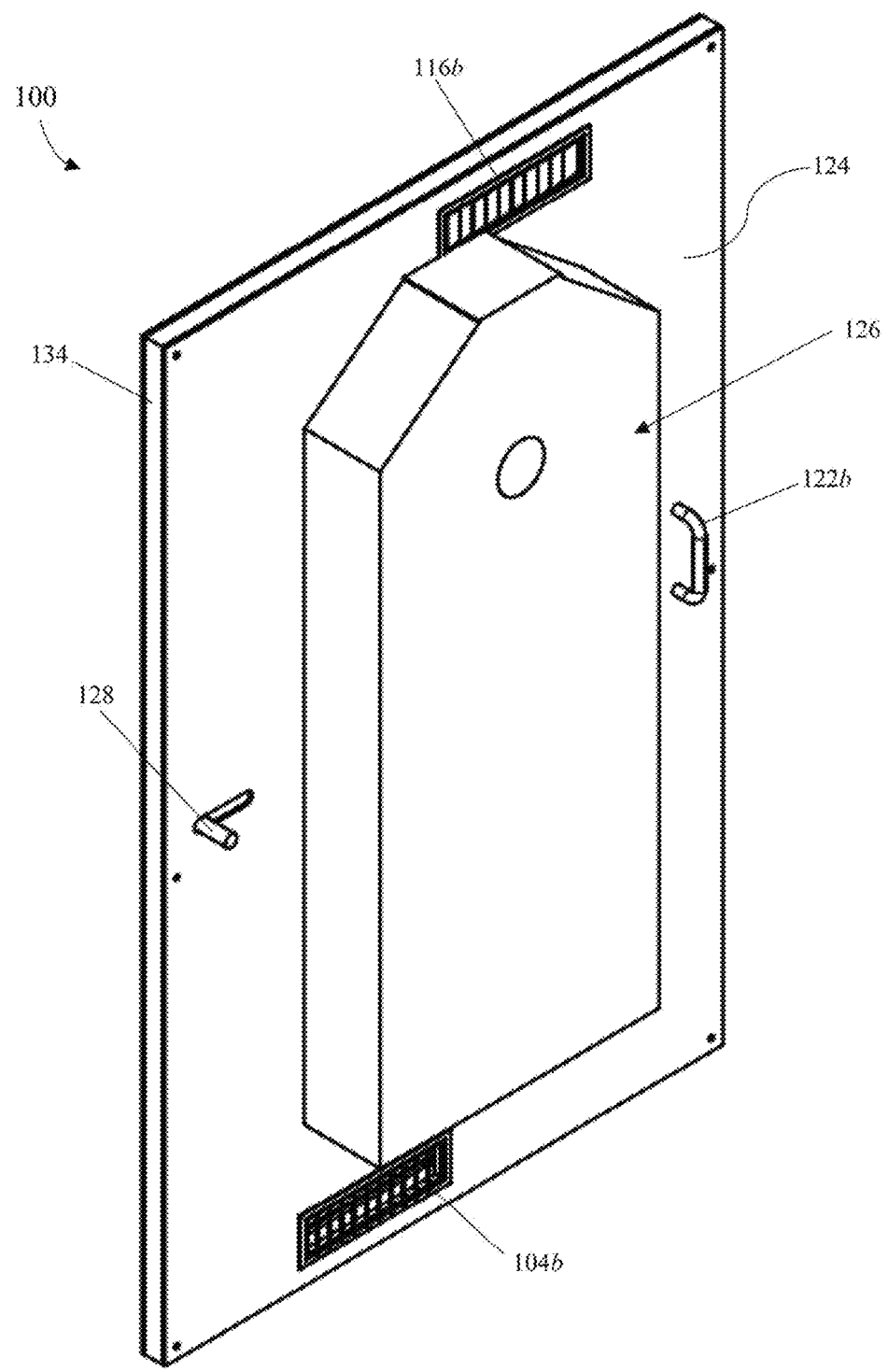
FIG. 2 is a rear perspective view of an indoor airborne pathogen control apparatus, in accordance with certain aspects of the present disclosure.
Figure 3:
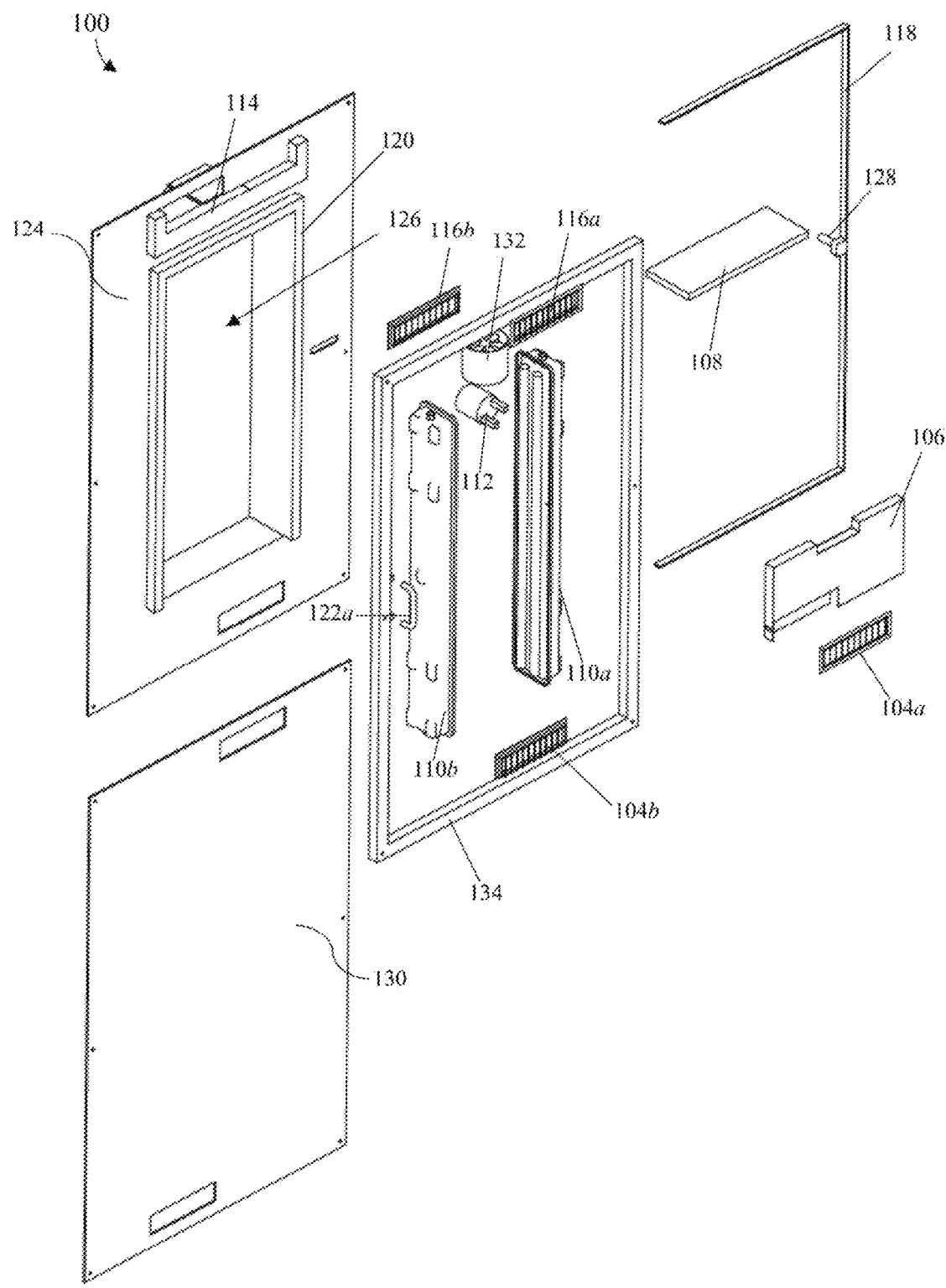
FIG. 3 is an exploded view of an indoor airborne pathogen control apparatus, in accordance with certain aspects of the present disclosure.

Turning now descriptively to the drawings, in which similar reference characters denote similar elements throughout the several views, FIGS. 1-3 depict various perspective and exploded views of an indoor airborne pathogen control apparatus 100. In accordance with certain aspects of the present disclosure, indoor airborne pathogen control apparatus 100 is configured as a door to be installed in a door frame for an interior room of a building (e.g., a hospital room). Indoor airborne pathogen control apparatus 100 may be utilized in hospitals and/or other controlled environments to control the relative atmospheric pressure of an interior room and clean/sanitize a volume of air within the interior room to prevent the spread of airborne pathogens and other microorganisms. In accordance with certain embodiments, indoor airborne pathogen control apparatus 100 may comprise an internal chamber 102 defined by a housing 126 comprising top, bottom and side walls extending laterally from and disposed on a rear door panel 124. A rear door panel 124 may be coupled to an inner frame 134 to define a rear surface of indoor airborne pathogen control apparatus 100 and a front door panel 130 may be coupled to an opposite side of inner frame 134 to define a front surface of indoor airborne pathogen control apparatus 100. A front door handle 122a may be coupled to a surface of front door panel 130 and a rear door handle 122b may be coupled to a surface of rear door panel 124 (opposite front door handle 122a) to define a handle for users to open and close indoor airborne pathogen control apparatus 100 when installed as an interior door in a building. A lower hood 106 comprising an intake duct may be disposed on a lower surface of rear door panel 124 and coupled to a lower portion of inner frame 134. Lower hood 106 may comprise an internal channel extending from a lower opening adjacent to inner frame 134 to an upper opening leading to internal chamber 102. A front intake vent 104a and/or a rear intake vent 104b may be coupled to a surface of lower hood 106 to define an air intake port. An upper hood 114 comprising an output duct may be disposed on an upper surface of rear door panel 124 and coupled to an upper portion of inner frame 134. Upper hood 114 may comprise an internal channel extending from a lower opening extending from internal chamber 102 to an upper opening adjacent to an upper portion of inner frame 134. In accordance with certain aspects of the present disclosure, indoor airborne pathogen control apparatus 100 may comprise an airflow path extending from the internal channel of lower hood 106 through internal chamber 102 and through the internal channel of upper hood 114 (as further shown and described in FIGS. 4A and 4B).

In accordance with certain aspects of the present disclosure, indoor airborne pathogen control apparatus 100 may further comprise a blower fan 132 (as shown in FIG. 3) comprising an electric motor operably engaged with a power source and configured to establish a directional flow of air upwards through internal chamber 102. When blower fan 132 is operably engaged, indoor airborne pathogen control apparatus 100 is configured to draw a volume of air from a surrounding interior environment via front intake vent 104a and lower hood 106 and into internal chamber 102 and output the volume of air via upper hood 114 and front output vents 116a or 116b back into the surrounding interior environment. In accordance with certain aspects of the present disclosure, the volume of air passed through internal chamber 102 is disinfected and sanitized prior to being outputted back into the surrounding interior environment. The volume of air passed through internal chamber 102 may be disinfected and sanitized according to one or more disinfection or germicidal treatment modalities. Indoor airborne pathogen control apparatus 100 may further comprise an air filter 108 disposed on a lower portion of housing 126 to cover an area comprising a lower opening of internal chamber 102 such that air drawn through lower hood 106 must be drawn through air filter 108 before reaching internal chamber 102. In certain embodiments, air filter 108 may comprise a high-efficiency particulate absorbing or high-efficiency particulate arrestance (HEPA) filter. Air filter 108 may comprise an internal filter substrate configured to filter passing airborne particles at an efficiency level of at least 99.0% of particles whose diameter is equal to 0.3 microns, such as pollen, dirt, dust, moisture, bacteria (0.2-2.0 microns), virus (0.02-0.3 microns), and submicron liquid aerosol (0.02-0.5 microns). In certain embodiments, air filter 108 may be constructed from, and/or impregnated with, one or more bactericidal and/or viricidal materials (e.g., silver or copper nanoparticles or the like) or substances (e.g., chemicals or essential oils). In certain embodiments, air filter 108 may be impregnated with a monoterpene phenol, such as thymol and/or carvacrol, to aid in damaging or inactivating airborne microorganisms. Thymol is a monoterpene phenol in the essential oil family and is a proven fungicide, medical disinfectant, tuberculocide, and virucide that is effective against pathogenic bacteria, fungi, and several viruses, including HIV-I. Thymol and its isomer carvacrol are hydrophobic organic compounds that penetrate cell walls and cell membranes increasing permeability so that there is a depolarization of the cytoplasmic membrane, a depletion of intracellular contents and an interruption in adenosine triphosphate production. These organic molecules also bind to the minor groove of DNA causing destabilization of the structure and inhibit cell replication. There are direct negative effects on viral structure which inhibit viral docking mechanisms impairing viral entry into cells. Development of resistance is not known to occur with exposure to these organic molecules.

In accordance with certain aspects of the present disclosure, indoor airborne pathogen control apparatus 100 may further comprise one or more UV-C emitter assembly 110a,b coupled to a vertical surface of housing 126 inside internal chamber 102. UV-C emitter assembly 110a,b may comprise one or more light-generating emitters configured to pulse an emission of ultraviolet radiation in the UV-C range; e.g., 200 nm-280 nm. In certain embodiments, the emitters may be configured to pulse an emission of radiation in the range of 250 nm to 270 nm, and more preferably in the range of 254 nm to 266 nm. In certain embodiments, the emitters may be configured to pulse an emission of radiation in the range of 220 nm to 230 nm, and more preferably in the range of 222 nm to 227 nm. UV-C emitter assembly 110a,b may comprise one or more emitter types, including electronic gas-discharge lamps, such as low-pressure mercury-vapor lamps, high-pressure mercury vapor lamps, xenon lamps, mercury-xenon lamps, pulsed-xenon lamps, and deuterium lamps, and light emitting diodes (LEDs) comprising semiconductors configured to emit light in the UV-C spectrum, and/or combinations thereof. UV-C emitter assembly 110a,b may comprise two or more emitters configured to pulse an emission or radiation at two or more primary wavelengths (i.e., a dual-band emission or multiband emission). In certain embodiments, UV-C emitter assembly 110a,b is configured to pulse an emission of UV-C radiation inside internal chamber 102 at one or more UV-C wavelengths to inactivate airborne bacteria, viruses, parasites and/or other RNA or DNA-based life forms. In certain embodiments, UV-C emitter assembly 110a,b may comprise at least one visible light emitter configured to emit visible light at near-UV wavelength in a range of 400 nm to 405 nm.

In accordance with certain aspects of the present disclosure, indoor airborne pathogen control apparatus 100 may further comprise a plasma generator 112 housed inside housing 126 and being disposed within internal chamber 102. Plasma generator 112 may be oriented adjacent to upper hood 114 such that a volume of air is moved across a dielectric barrier of plasma generator 112 before being discharged through upper hood 114 and output vent 116a,b. In certain embodiments, plasma generator 112 may comprise a dielectric barrier operably configured to discharge cold plasma as a decontaminating oxidant. A dielectric barrier may be created by passing a gas through an electric diode that excites electrons without changing the temperature of the protons of neutrons. This unstable state can decontaminate the air by the process of reactive oxygen and nitrogen species and hydroxyl radical formation and nitric oxides oxidizing prokaryotic cells and viral DNA and RNA. There are three primary mechanisms by which cold plasma inactivates microbes. The first is the chemical interaction of radicals (0, OH), reactive species, or charged particles with cell membranes; the second is by damage to membranes and internal cellular components by UV photons; and the third is breaking of DNA strands by UV photons generated during recombination of the plasma species.

In accordance with certain aspects of the present disclosure, indoor airborne pathogen control apparatus 100 may further comprise a slide frame 118 slidably coupled to a surface of indoor airborne pathogen control apparatus 100 (e.g., rear door panel 124). Slide frame 118 may comprise a slide frame handle 128 configured to enable a user to move slide frame 118 laterally from left to right and vice versa. In certain embodiments, slide frame handle 128 may extend through an aperture of rear door panel 124. Slide frame 118 may comprise an upper frame arm and a lower frame arm. The upper frame arm may extend laterally through an aperture of upper hood 114 and the lower frame arm may extend laterally through an aperture of lower hood 106. The upper arm of slide frame 118 may be configured to configure front output vent 116a and rear output vent 116b between a first configuration and a second configuration in response to a user laterally sliding slide frame handle 128 between a first position and a second position. The lower arm of slide frame 118 may be configured to configure front intake vent 104a and rear intake vent 104b between a first configuration and a second configuration in response to a user laterally sliding slide frame handle 128 between a first position and a second position. In accordance with certain embodiments, slide frame 118 may be operably engaged with front output vent 116a, rear output vent 116b, front intake vent 104a and rear intake vent 104b to configure one or more airflow paths for indoor airborne pathogen control apparatus 100 (e.g., from front intake vent 104a to front output vent 116a; from front intake vent 104a to rear output vent 116b; from rear intake vent 104b to front output vent 116a; from rear intake vent 104b to rear output vent 116b).

Referring now to FIGS. 4A and 4B, functional diagrams of an indoor airborne pathogen control apparatus 400 in a first configuration 400a and a second configuration 400b are shown. In accordance with certain aspects of the present disclosure, indoor airborne pathogen control apparatus 400 may comprise indoor airborne pathogen control apparatus 100, as shown and described in FIGS. 1-3. Indoor airborne pathogen control apparatus 400 may be configured as an entry/exit door to an interior room of a building (e.g., a hospital room door in a hospital). In accordance with certain aspects of the present disclosure, indoor airborne pathogen control apparatus 400 may be configured in first configuration 400a to establish an airflow path via which a volume of air is drawn from a lower area of an interior room and is cleaned and disinfected before being discharged at an upper area of the interior room. Indoor airborne pathogen control apparatus 400 may be configured in second configuration 400b to establish an airflow path via which a volume of air is drawn from a lower area of an interior room at a first side of the indoor airborne pathogen control apparatus 400 and is cleaned and disinfected before being discharged at an upper area of an interior room at a second side of the indoor airborne pathogen control apparatus 400 (i.e., an opposite side).

Referring now to FIG. 4A, indoor airborne pathogen control apparatus 400 may be configured in first configuration 400a to establish an airflow pattern in an interior room to control/mitigate the dissemination/transmission of airborne contaminates within the interior room by drawing air downward, away from the breathing level of occupants of the room, and into an air intake at the floor level of indoor airborne pathogen control apparatus 400. In accordance with certain embodiments, a blower fan 412 is housed in an interior chamber 420 of housing 402. Blower fan 412 may comprise a single or multi-speed electric motor configured to selectively spin a fan blade to establish a directional airflow from a lower area of interior chamber 420 (i.e., an area below blower fan 412) to an upper area of interior chamber 420 (i.e., an area above blower fan 412). In accordance with certain aspects of the present disclosure, directional air vents 404a,b may be disposed on a lower area of housing 402 comprising an intake duct 406. Directional air vents 404a,b may be configured to be opened and closed to enable or restrict airflow therethrough. In certain embodiments, indoor airborne pathogen control apparatus 400 may comprise one or more dampers configured to selectively open/enable or close/block a flow of air through directional air vents 404a,b. As shown in first configuration 400a, directional air vent 404a is configured in an open configuration to receive an intake of air therethrough and directional air vent 404b is configured in a closed configuration to block an intake of air therethrough. In accordance with various aspects of the present disclosure, a HEPA filter 408 is disposed in an area of interior chamber 420 such that an airflow is drawn through HEPA filter 408 from intake duct 406 and into interior chamber 420. In certain embodiments, HEPA filter 408 comprises air filter 108, as shown and described in FIGS. 1-3. In certain embodiments, indoor airborne pathogen control apparatus 400 comprises a first UV-C emitter assembly 418a and a second UV-C emitter assembly 418b housed within housing 402. In certain embodiments, UV-C emitter assemblies 418a,b may be configured UV-C emitter assemblies 110a,b, as shown and described in FIGS. 1-3. UV-C emitter assemblies 418a,b may be configured to pulse an emission of UV-C radiation within the interior area of interior chamber 420. The emission of UV-C radiation may comprise one or more wavelengths known to exhibit a strong germicidal effect when applied to airborne microorganisms. In accordance with certain aspects of the present disclosure, indoor airborne pathogen control apparatus 400 is configured to establish an airflow such that a volume of air is drawn through HEPA filter 408 and is exposed to an emission of UV-C radiation from UV-C emitter assemblies 418a,b while passing through the interior area of interior chamber 420. In accordance with various aspects of the present disclosure, an indoor airborne pathogen control apparatus 400 further comprises a plasma generator 410 housed within interior chamber 420. In certain embodiments, plasma generator 410 comprises plasma generator 112, as shown and described in FIGS. 1-3. In accordance with certain aspects of the present disclosure, plasma generator 410 comprises a dielectric barrier configured to discharge cold plasma as a decontaminating oxidant. In accordance with certain embodiments, indoor airborne pathogen control apparatus 400 is configured to establish an airflow such that a volume of air is drawn over an electric diode of plasma generator 410, which excites the electrons in the passing air molecules without changing the temperature of the protons or neutrons. This unstable state decontaminates the passing air by the process of reactive oxygen and nitrogen species and hydroxyl radical formation and nitric oxides oxidizing prokaryotic cells and viral DNA and RNA. In accordance with certain aspects of the present disclosure, indoor airborne pathogen control apparatus 400 is configured to establish an airflow such that a volume of air is drawn across a surface of plasma generator 410 and forced into output duct 416 via blower 412. As shown in first configuration 400a, directional air vent 414a is configured in an open configuration to establish a supply/output vent for output duct 416. As shown in first configuration 400a, directional air vent 404b is configured in a closed configuration to block air from flowing through output duct 416 at one side such that clean/disinfected air is discharged from interior chamber 420 via directional air vent 414a.

Referring now to FIG. 4B, indoor airborne pathogen control apparatus 400 may be configured in second configuration 400b to direct a flow of air to or from an interior room to increase or decrease the relative atmospheric pressure of the interior room to create a positive pressure or negative pressure environment. As shown in second configuration 400b, directional air vent 404a is configured in an open configuration to receive an intake of air therethrough and directional air vent 404b is configured in a closed configuration to block an intake of air therethrough. Blower fan 412 is configured to establish an airflow through interior chamber 420 in the same manner as described in FIG. 4A. As shown in second configuration 400b, directional air vent 414b is configured in an open configuration to establish a supply/output vent for output duct 416. Directional air vent 404a is configured in a closed configuration to block air from flowing through output duct 416 at one side such that clean/disinfected air is discharged from interior chamber 420 via directional air vent 414b.

Figure 5:
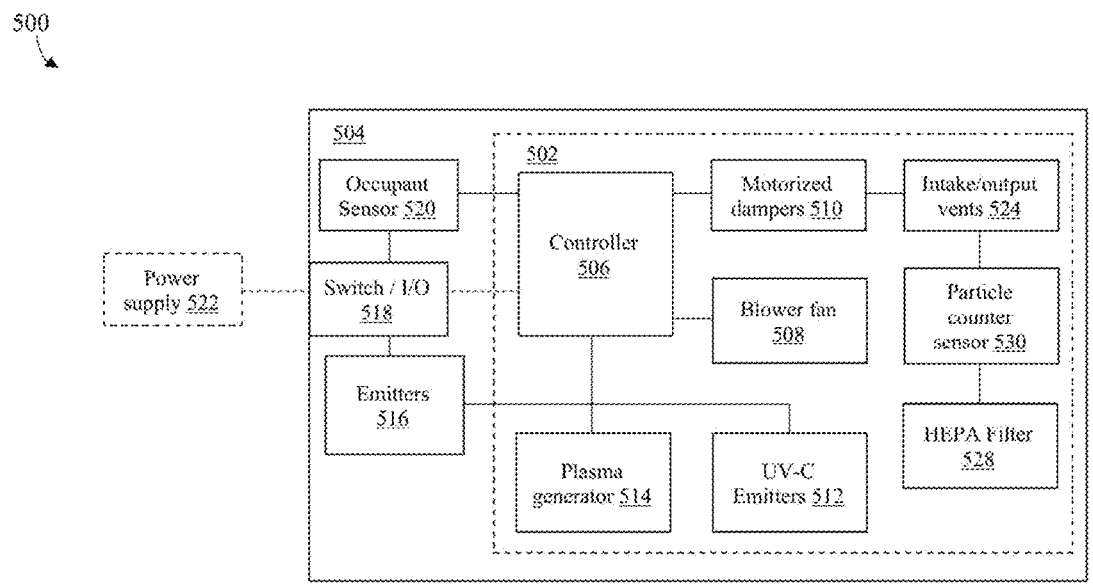
FIG. 5 is a functional block diagram of an indoor airborne pathogen control system, in accordance with certain aspects of the present disclosure.

Referring now to FIG. 5, a functional block diagram of an indoor airborne pathogen control system 500 is shown. In accordance with certain embodiments, indoor airborne pathogen control system 500 may comprise door assembly 502 and a door frame assembly 504. Door assembly 502 may comprise indoor airborne pathogen control apparatus 100, as shown and described in FIGS. 1-3. In accordance with certain aspects of the present disclosure, door assembly 502 may be configured to establish a flow of air through an interior chamber of door assembly 502, as shown and described in FIGS. 4A and 4B. Door assembly 502 may be coupled to door frame assembly 504 via one or more hinges to enable door assembly 502 to open and close within door frame assembly 504. In accordance with certain embodiments, door assembly 502 may comprise a controller 506 operably engaged with a blower fan 508, one or more UV-C emitters 512, and a plasma generator 514. In certain embodiments, one or more motorized dampers 510 may be operably engaged with controller 506 to regulate a flow of air into or out of one or more vents 524. Motorized dampers 510 may be configured to completely and/or partially block a flow of air into or out of one or more vents 524 to enable one or more airflow patterns through an interior chamber of door assembly 502 (e.g., as shown and described in FIGS. 4A and 4B). Door assembly 502 may further comprise a HEPA filter 528 disposed in the interior chamber of door assembly 502 to filter airborne particles from a volume of air drawn through the interior chamber of door assembly 502 via blower fan 508. In certain embodiments, blower fan 508 is a multi-speed fan configured to establish a variable airflow output (e.g., cubic feet per minute) through the interior chamber of door assembly 502. Door assembly 502 may further comprise a particle counter sensor 530. In certain embodiments, particle counter sensor 530 may be positioned adjacent or proximal to an output vent of one or more vents 524, such that a volume of air passing over particle counter sensor 530 has already passed through HEPA filter 528 and been exposed to an output of UV-C emitters 512 and plasma generator 514. In certain embodiments, particle counter sensor 530 may comprise an airborne particle counter comprising a laser diode, a collecting lens and a photodetector. Particle counter sensor 530 may be configured to detect scattered light from the laser diode projected on the collecting lens and convert the scattered light into an electrical pulse to count airborne particles passing through the airborne particle counter. Particle counter sensor 530 may be communicably engaged with controller 506 to communicate a sensor input comprising airborne particle data. Controller 506 may be configured to process the sensor input to determine a measure of airborne particles present in the output air supplied from the interior chamber of door assembly 502.

In accordance with certain aspects of the present disclosure, door frame assembly 504 may comprise a switch or input/output (I/O) interface 518 operably engaged with controller 506 to selectively deliver a flow of power from a power supply 522 (e.g., a wireline electrical supply) to controller 506. In certain embodiments, switch 518 may be engaged/disengaged in response to opening/closing door assembly 502 such that controller 506 may be configured to deliver a flow of power to one or more of blower fan 508, UV-C emitter 512 and/or plasma generator 514 when door assembly 502 is in a closed position and disengage a flow of power to one or more of the same when door assembly 502 is in an open position. In certain embodiments, door frame assembly 504 may further comprise one or more emitters 516 and an occupant sensor 520. Emitters 516 and occupant sensor 520 may be operably engaged with controller 506 and/or switch or input/output (I/O) interface 518 to be selectively engaged in one or more mode of operation. In certain embodiments, emitters 516 may comprise one or more UV-C emitters (e.g., emitters configured to emit UV-C light at a primary wavelength between 200 nm-280 nm) and/or one or more near-UV emitters (e.g., emitters configured to emit visible light at a primary wavelength between 400 nm-405 nm). In accordance with certain aspects of the present disclosure, controller 506 may be configured to engage emitters 516 to pulse an emission of radiation in response to door assembly 502 being configured in an open position and terminate the emission of radiation in response to door assembly 502 being configured in a closed position.

In accordance with certain embodiments, emitters 516 may be configured at one or more points along a surface of door frame assembly 504 to generate a curtain of light comprising a zone of emission covering an entire opening of door frame assembly 504, such that any air and/or object that passes through the opening of door frame assembly 504 is exposed to the emission of radiation from emitters 516. In accordance with further aspects of the present disclosure, occupant sensor 520 may be configured to detect the presence of an occupant within an emission range of emitters 516 and provide a sensor input to controller 506 in response to the same. Controller 506 may be configured to terminate the emission of radiation from emitters 516 in response to processing an input from occupant sensor 520 indicative of the presence of an occupant within an emission range of emitters 516 exceeding a specified radiation exposure threshold.

Figure 6:
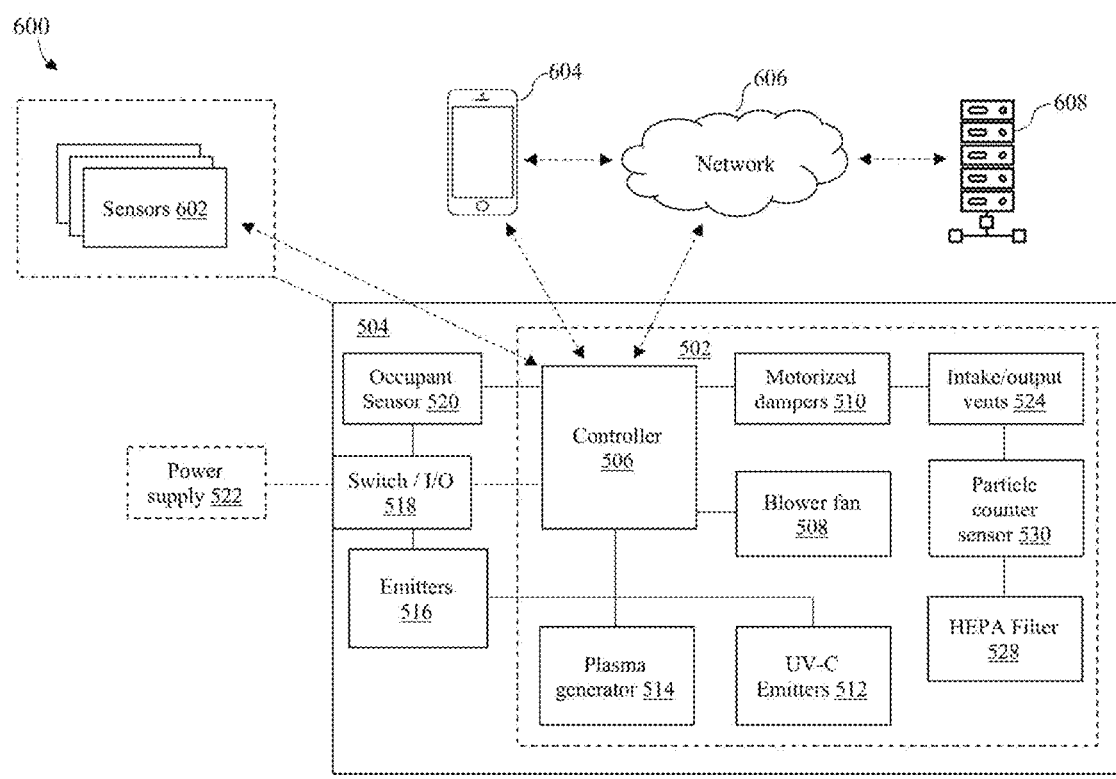
FIG. 6 is a functional block diagram of an indoor airborne pathogen control system, in accordance with certain aspects of the present disclosure.

Referring now to FIG. 6, a functional block diagram of an indoor airborne pathogen control system 600 is shown. In accordance with certain aspects of the present disclosure, indoor airborne pathogen control system 600 may comprise door assembly 502 and door frame assembly 504, as shown and described in FIG. 5. In accordance with certain aspects of the present disclosure, door assembly 502 may be configured as indoor airborne pathogen control apparatus 100, as shown and described in FIGS. 1-3. In accordance with certain aspects of the present disclosure, door assembly 502 may be configured to establish a flow of air through an interior chamber of door assembly 502, as shown and described in FIGS. 4A and 4B. In accordance with certain aspects of the present disclosure, indoor airborne pathogen control system 600 may comprise indoor airborne pathogen control system 500 as well as additional elements comprising one or more sensors 602, at least one mobile electronic device 604, and at least one networked server 608. In certain embodiments, mobile electronic device 604 may be communicably engaged with controller 506 via a wireless or wireline communications interface and/or a network communications interface via a communications network 606 (e.g., an Internet connection). Networked server 608 may be communicably engaged with controller 506 via communications network 606.

In accordance with certain aspects of the present disclosure, sensors 602 may be communicably engaged with controller 506 via one or more wireless or wired data transfer interface. Sensors 602 may comprise one or more of a camera, such as a digital video or digital still image camera, an acoustic transducer, a radiation sensor, a particle counter sensor, an occupant sensor, such as a passive infrared sensor, and environmental sensors, such as particle counter sensors, pressure sensors, temperature and humidity sensors, and CO2 sensors or other sensors configured detect a change in an environment due to the presence of a human occupant. In certain embodiments, sensors 602 may comprise one or more body-worn radiation sensors configured to measure a total dose of UV-C radiation received by the wearer within a given time period (e.g., an OSHA threshold during a work shift). Sensors 602 may comprise one or more sensors configured to detect one or more conditions within an interior environment within a vicinity of door assembly 502 and communicate such signals as inputs to controller 506. Controller 506 may be configured to receive and process sensor inputs according to one or more data processing framework to engage one or more operational modes of door assembly 502 and/or door frame assembly 504 and/or invoke one or more communication protocols between controller 506, mobile electronic device 604 and/or networked server 608. In accordance with certain aspects of the present disclosure, mobile electronic device 604 may be communicably engaged with controller 506 to send and/or receive one or more data packets to and/or from controller 506. In certain embodiments, mobile electronic device 604 may comprise a user interface configured to enable a user to input and/or otherwise configure one or more commands, settings and/or operational controls/modes of controller 506. In certain embodiments, controller 506 may be configured to communicate system data to mobile electronic device 604 and/or networked server 608, such as sensor data (e.g., sensor measurements received from sensors 602), operational data (e.g., status of HEPA filter 528) and/or other system activity data (e.g., runtime of blower fan 508, configuration of intake/output vents 524), according to one or more communication protocols and/or one or more requests from mobile electronic device 604 and/or networked server 608.

Figure 7:
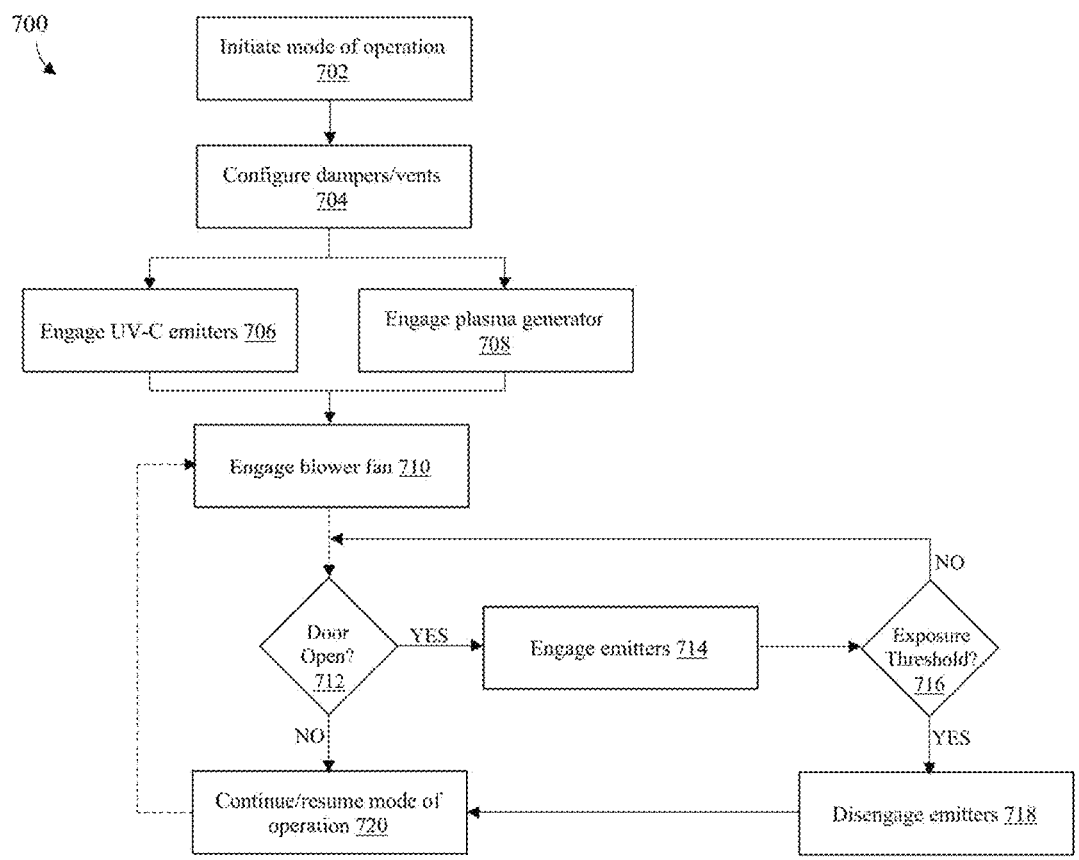
FIG. 7 is a process flow diagram of a routine of an indoor airborne pathogen control system, in accordance with certain aspects of the present disclosure.

Referring now to FIG. 7, a process flow diagram of a routine 700 of an indoor airborne pathogen control system is shown. In accordance with certain aspects of the present disclosure, routine 700 may comprise, or otherwise be embodied within, one or more routines or sub-routine of indoor airborne pathogen control system 500 (as shown in FIG. 5) and/or one or more routines or sub-routines of indoor airborne pathogen control system 600 (as shown in FIG. 6). In accordance with certain aspects of the present disclosure, routine 700 may be embodied as one or more processor-executable instructions stored in a local or remote memory device that, when executed, command one or more operations of controller 506 (as shown in FIGS. 5-6) and/or mobile electronic device 604 (as shown in FIG. 6) and/or networked server 608 (as shown in FIG. 6).

In accordance with certain aspects of the present disclosure, routine 700 may be initiated upon executing one or more steps or operations to initiate a mode of operation for an indoor airborne pathogen control system (Step 702). In certain embodiments, initiating a mode of operation for an indoor airborne pathogen control system may comprise one or more steps for engaging an operational mode of door assembly 502 and/or door frame assembly 504 (as shown and described in FIG. 5). In certain embodiments, routine 700 may proceed by executing one or more steps or operations to configure one or more intake/output vents and/or dampers to establish a directional airflow pattern between an air intake vent and an air output vent of the indoor airborne pathogen control system (Step 704). In certain embodiments, one or more intake vents may comprise front intake vent 104a and rear intake vent 104b and one or more output vents may comprise front output vent 116a and rear output vent 116b. Step 704 may comprise manually configuring one or more intake/output vents (e.g., as described in FIGS. 1-3) and/or may comprise engaging one or more motorized controls, such as a motorized vent or motorized damper to open/close the one or more intake/output vents. In certain embodiments, Step 704 may comprise one or more steps or operations for partially opening/closing the one or more intake/output vents and/or dampers to modify/control a volume and rate (i.e., cubic feet per minute) at one or both of an air intake or air output of the indoor airborne pathogen control system. In accordance with certain embodiments, routine 700 may proceed by executing one or more steps or operations for engaging a plurality of UV-C emitters housed within an internal chamber of indoor airborne pathogen control system (e.g., internal chamber 102 of indoor airborne pathogen control apparatus 100, as shown and described in FIGS. 1-3) (Step 706). Routine 700 may further proceed by executing one or more steps or operations for engaging a plasma generator housed within the internal chamber of indoor airborne pathogen control system (e.g., plasma generator 112 of indoor airborne pathogen control apparatus 100, as shown and described in FIGS. 1-3) (Step 708). Routine 700 may further proceed by executing one or more steps or operations for engaging a blower fan housed within the internal chamber of indoor airborne pathogen control system (e.g., plasma generator 132 of indoor airborne pathogen control apparatus 100, as shown and described in FIGS. 1-3) (Step 710). In certain embodiments, Step 710 may further comprise executing one or more steps or operations for establish a fan speed of the blower fan. In accordance with certain aspects of the present disclosure, routine 700 may further proceed by executing one or more operations to determine whether a door assembly of indoor airborne pathogen control system is configured in an open position (Step 712). In certain embodiments, a position of the door assembly may be established automatically upon releasing or engaging a switch in response to an occupant opening and/or closing the door assembly. In some embodiments, the position of the door assembly may be established by the controller in response to processing one or more sensor inputs received in response to an occupant opening and/or closing the door assembly. In accordance with certain aspects of the present disclosure, if the door assembly is configured in a closed position (NO), routine 700 may continue its present mode of operation (Step 720). If the door assembly is configured in an open position (YES), routine 700 may proceed by executing one or more steps or operations for engaging one or more emitters disposed around a surface of a door frame assembly (e.g., door frame assembly 504, as shown and described in FIG. 5) to establish a curtain of light/radiation over an entirety of an opening of the door frame assembly (Step 714). In accordance with certain embodiments, routine 700 may further comprise executing one or more steps or operations for determining whether a UV-C exposure threshold has been reached for one or more occupants of an interior environment (Step 716). If YES, routine 700 may comprise one or more steps or operations for disengaging the one or more emitters disposed around a surface of a door frame assembly (Step 718) and/or one or more steps for continuing/resuming an existing mode of operation (Step 720). If NO, routine 700 may comprise one or more steps or operations for continuing to engage the emitters in accordance with Step 714 until the door assembly is returned to the closed position or the output of step 716 is indicative of a UV-C exposure threshold being reached for one or more occupants of the internal environment.

Figure 8:
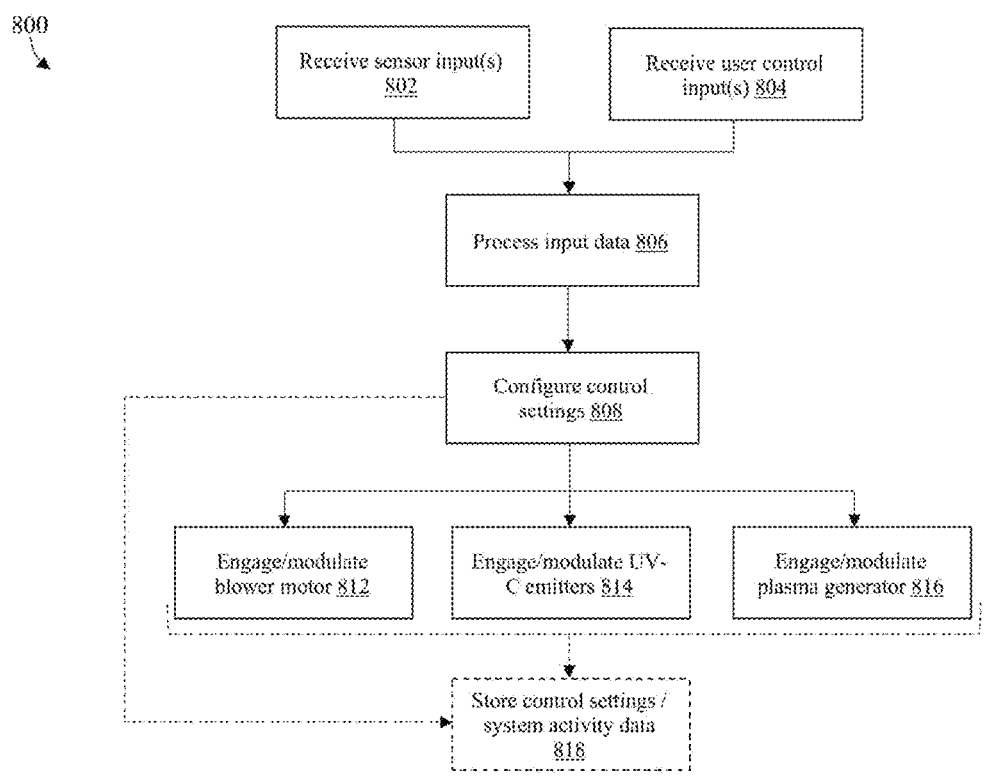
FIG. 8 is a process flow diagram of a routine of an indoor airborne pathogen control system, in accordance with certain aspects of the present disclosure.

Referring now to FIG. 8, a process flow diagram of a routine 800 of an indoor airborne pathogen control system is shown. In accordance with certain aspects of the present disclosure, one or more steps or operations of routine 800 may be sequential or conditional to one or more steps or operations of routine 700 and/or may comprise one or more sub-steps or sub-routines of routine 700. Routine 800 may comprise, or otherwise be embodied within, one or more system routines or sub-routines of indoor airborne pathogen control system 500 (as shown in FIG. 5) and/or one or more system routines or sub-routines of indoor airborne pathogen control system 600 (as shown in FIG. 6). In accordance with certain aspects of the present disclosure, routine 800 may be embodied as one or more processor-executable instructions stored in a local or remote memory device that, when executed, command one or more operations of controller 506 (as shown in FIGS. 5-6) and/or mobile electronic device 604 (as shown in FIG. 6) and/or networked server 608 (as shown in FIG. 6).

In accordance with certain aspects of the present disclosure, routine 800 may be initiated by executing one or more steps or operations for receiving one or more sensor inputs from one or more sensors (e.g., sensors 602, as shown in FIG. 6) (Step 802) and receiving one or more user control inputs from a user control interface (e.g., input/output (I/O) interface 518 and/or mobile electronic device 604, as shown in FIGS. 5-6) (Step 804). Routine 800 may proceed by executing one or more steps or operations for processing the input data from Steps 802 and/or 804 via an integral controller of the indoor airborne pathogen control system and/or a mobile electronic device and/or a networked server (Step 806). Routine 800 may proceed by executing one or more steps or operations for configuring one or more control settings of the indoor airborne pathogen control system in response to processing the input data from Steps 802 and/or 804 (Step 808). In accordance with certain aspects of the present disclosure, an output of Step 808 may be utilized to update and/or configure one or more logic, rules or instructions stored in a local or remote memory device of the controller and/or the mobile electronic device and/or the networked server (Step 818). In accordance with certain aspects of the present disclosure, routine 800 may proceed by executing one or more steps or operations for engaging and/or modulating one or more components of the indoor airborne pathogen control system, including but not limited to a blower motor (Step 812), one or more UV-C emitters (Step 814) and a plasma generator (Step 816). In accordance with certain aspects, routine 800 may comprise one or more steps or operations for dynamically modulating one or more of the fan blower motor, the UV-C emitters and/or the plasma generator in response to one or more real-time sensor inputs (Step 802) and/or user control inputs (Step 804). In accordance with certain embodiments, routine 800 may proceed by executing one or more steps or operations for storing the control settings (as configured in step 808) and/or storing system activity data for one or more of the fan blower motor, the UV-C emitters and/or the plasma generator in a local or remote memory device of the controller and/or the mobile electronic device and/or the networked server (Step 818).

Figure 9:
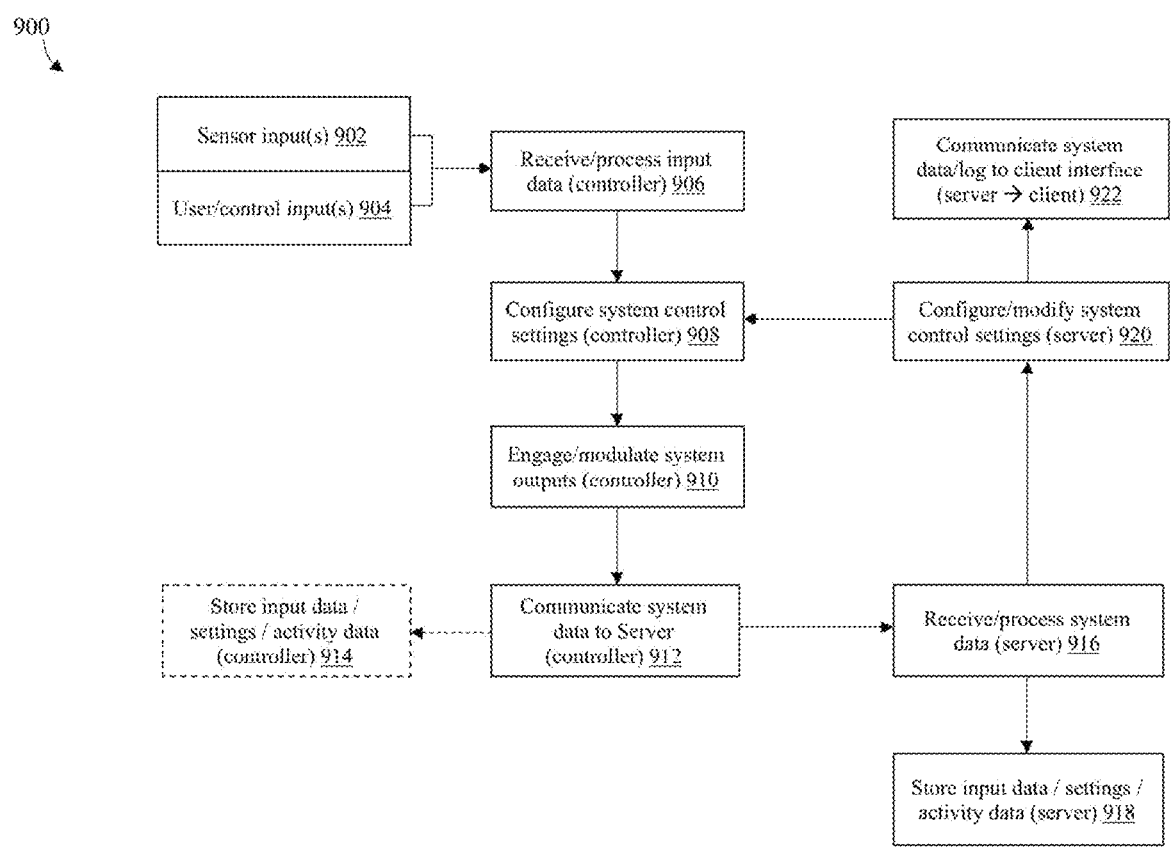
FIG. 9 is a process flow diagram of a routine of an indoor airborne pathogen control system, in accordance with certain aspects of the present disclosure.

Referring now to FIG. 9, a process flow diagram of a routine of an indoor airborne pathogen control system is shown. In accordance with certain aspects of the present disclosure, one or more steps or operations of routine 900 may be sequential or conditional to one or more steps or operations of routine 800 and/or routine 700 and/or may comprise one or more sub-steps or sub-routines of routine 800 and/or routine 700. Routine 900 may comprise, or may otherwise be embodied within, one or more system routines or sub-routines of indoor airborne pathogen control system 500 (as shown in FIG. 5) and/or one or more system routines or sub-routines of indoor airborne pathogen control system 600 (as shown in FIG. 6). In accordance with certain aspects of the present disclosure, routine 900 may be embodied as one or more processor-executable instructions stored in a local or remote memory device that, when executed, command one or more operations of controller 506 (as shown in FIGS. 5-6) and/or mobile electronic device 604 (as shown in FIG. 6) and/or networked server 608 (as shown in FIG. 6).

In accordance with certain aspects of the present disclosure, routine 900 may be initiated upon receiving one or more sensor inputs 902 and/or one or more user/control inputs 904 and processing the one or more inputs at a controller of the indoor airborne pathogen control system (Step 906). In accordance with certain embodiments, the one or more sensor inputs 902 may comprise inputs from sensors 602 (as shown and described in FIG. 6). The one or more user/control inputs 904 may comprise one or more inputs received from mobile electronic device 604 and/or networked server 608 (as shown in FIG. 6) and/or I/O interface 518 (as shown in FIG. 5). In accordance with certain embodiments, routine 900 may proceed by executing one or more steps or operations for configuring one or more control settings at the controller of the indoor airborne pathogen control system (Step 908). Routine 900 may proceed by executing one or more steps or operations for engaging or modulating one or more system components of the indoor airborne pathogen control system in response to an output of Step 908 (Step 910). In accordance with certain embodiments, the one or more system components may comprise one or more of a fan blower motor, a vent damper, one or more UV-C or visible light emitters and/or a plasma generator. Routine 900 may proceed by executing one or more steps or operations for communicating system activity data from the controller to a networked server (Step 912). In accordance with certain embodiments, Step 912 may comprise one or more steps or operations for communicating system activity data from the controller to a mobile electronic device. In accordance with certain embodiments, Step 912 may include one or more communications protocols for establishing a data transfer interface between the controller and the networked server and/or the controller and the mobile electronic device. In accordance with certain embodiments, routine 900 may comprise one or more steps or operations for storing, with the controller, one or more of the input data, system settings/control data, and system activity data in a local or remote memory device of the controller and/or the mobile electronic device and/or the networked server (Step 914). In accordance with certain aspects of the present disclosure, routine 900 may further comprise one or more steps or operations for receiving, at the networked server, one or more of the input data, system settings/control data, and system activity data and processing the received data according to one or more data processing framework (Step 916). In accordance with certain embodiments, Step 916 may comprise one or more steps or operations for receiving and processing the input/activity data at the mobile electronic device. In accordance with certain embodiments, routine 900 may comprise one or more steps or operations for storing, with the networked server, one or more of the input data, system settings/control data, and system activity data in a local or remote memory device (Step 918). In accordance with certain embodiments, routine 900 may further comprise executing one or more steps or operations at the networked server for configuring or modifying one or more system/control settings for the indoor airborne pathogen control system and communicating the updated/modified system/control settings to the controller via a network communications interface (Step 920). In accordance with certain aspects of the present disclosure, routine 900 may further comprise one or more steps or operations for communicating system activity data and/or audit log data to a user interface of a mobile electronic device via the network communications interface (Step 922).

Figure 10:
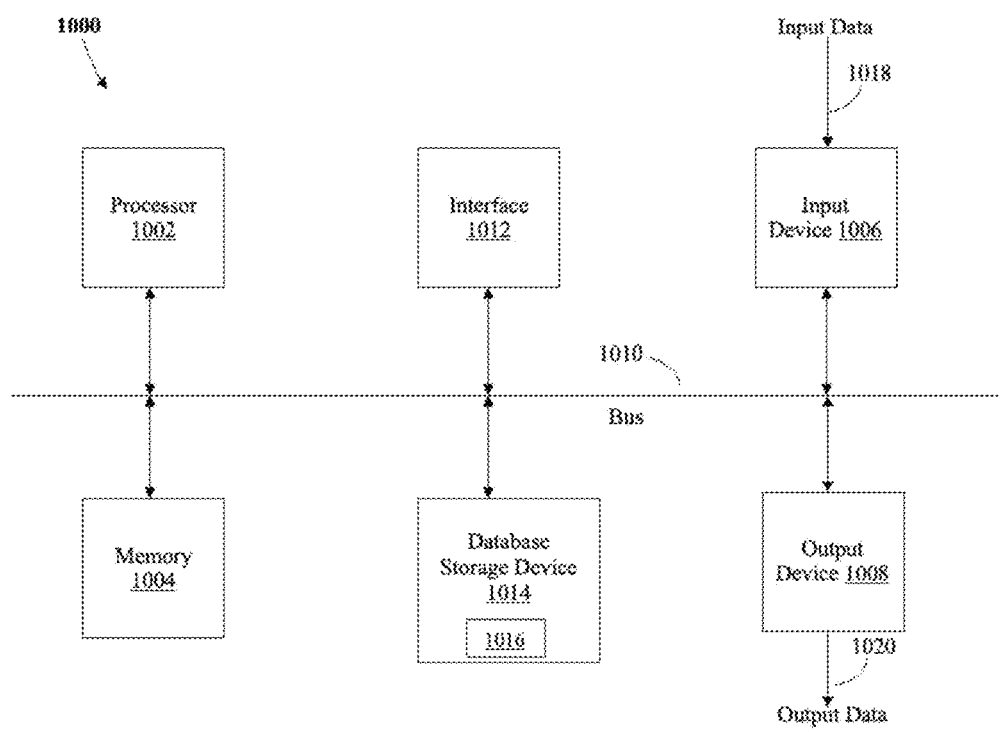
FIG. 10 is a block diagram of a processor-implemented computing device in which one or more aspects of the present disclosure may be implemented.

Referring now to FIG. 10, a processor-implemented computing system 1000 in which one or more aspects of the present disclosure may be implemented is shown. In accordance with certain aspects of the present disclosure, processing system 1000 may be configured as one or more of controller 506 (as shown in FIGS. 5-6), mobile electronic device 604 and/or networked server 608 (as shown in FIG. 6). According to an embodiment, a processing system 1000 may generally comprise at least one processor 1002, or processing unit or plurality of processors, memory 1004, at least one input device 1006 and at least one output device 1008, coupled together via a bus or group of buses 1010. In certain embodiments, input device 1006 and output device 1008 could be the same device. An interface 1012 can also be provided for coupling the processing system 1000 to one or more peripheral devices, for example interface 1012 could be a PCI card or PC card. At least one storage device 1014 which houses at least one database 1016 can also be provided. The memory 1004 can be any form of memory device, for example, volatile or non-volatile memory, solid state storage devices, magnetic devices, etc. The processor 1002 could comprise more than one distinct processing device, for example to handle different functions within the processing system 1000. Input device 1006 receives input data 1018 and can comprise, for example, a keyboard, a pointer device such as a pen-like device or a mouse, audio receiving device for voice-controlled activation such as a microphone, data receiver or antenna such as a modem or wireless data adaptor, data acquisition card, etc. Input data 1018 could come from different sources, for example keyboard instructions in conjunction with data received via a network. Output device 1008 produces or generates output data 1020 and can comprise, for example, a display device or monitor in which case output data 1020 is visual, a printer in which case output data 1020 is printed, a port for example a USB port, a peripheral component adaptor, a data transmitter or antenna such as a modem or wireless network adaptor, etc. Output data 1020 could be distinct and derived from different output devices, for example a visual display on a monitor in conjunction with data transmitted to a network. A user could view data output, or an interpretation of the data output, on, for example, a monitor or using a printer. The storage device 1014 can be any form of data or information storage means, for example, volatile or non-volatile memory, solid state storage devices, magnetic devices, etc.

In use, the processing system 1000 is adapted to allow data or information to be stored in and/or retrieved from, via wired or wireless communication means, at least one database 1016. The interface 1012 may allow wired and/or wireless communication between the processing unit 1002 and peripheral components that may serve a specialized purpose. In general, the processor 1002 can receive instructions as input data 1018 via input device 1006 and can display processed results or other output to a user by utilizing output device 1008. More than one input device 1006 and/or output device 1008 can be provided. It should be appreciated that the processing system 1000 may be any form of terminal, server, specialized hardware, or the like.

It is to be appreciated that the processing system 1000 may be a part of a networked communications system. Processing system 1000 could connect to a network, for example the Internet or a WAN. Input data 1018 and output data 1020 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 1000 illustrated in FIG. 10 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 10 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 1000 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 1000, or portions thereof, may be stored in a remote memory storage device. It is to be appreciated that the illustrated network connections of FIG. 10 are exemplary and other means of establishing a communications link between multiple computers may be used.

FIG. 10 is intended to provide a brief, general description of an illustrative and/or suitable exemplary environment in which embodiments of the below described present invention may be implemented. FIG. 10 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system environment 1000 of FIG. 10. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Figure 11A:
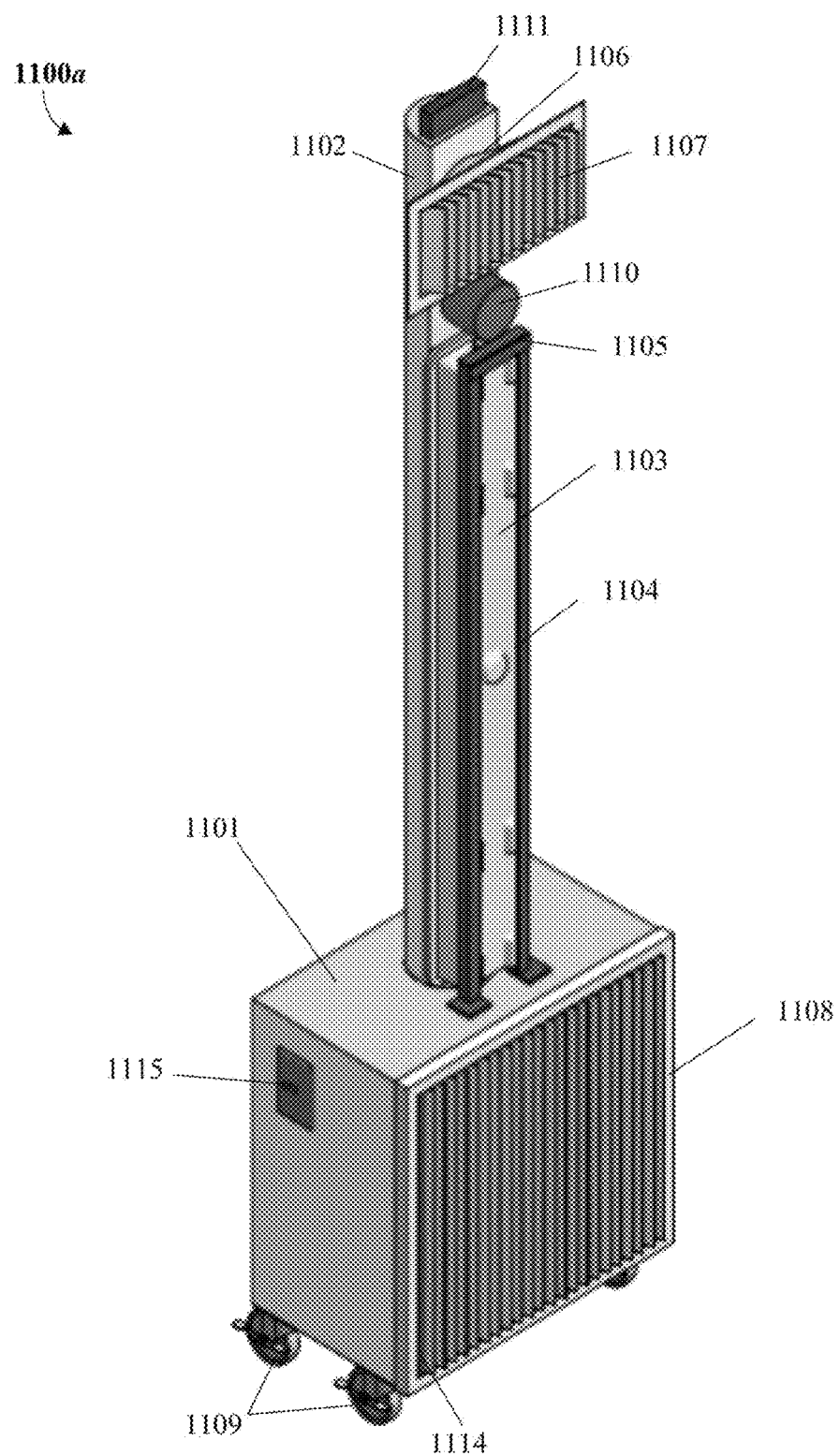
FIG. 11A is a perspective view of a portable airborne pathogen control apparatus, in accordance with certain aspects of the present disclosure.
Figure 11B:
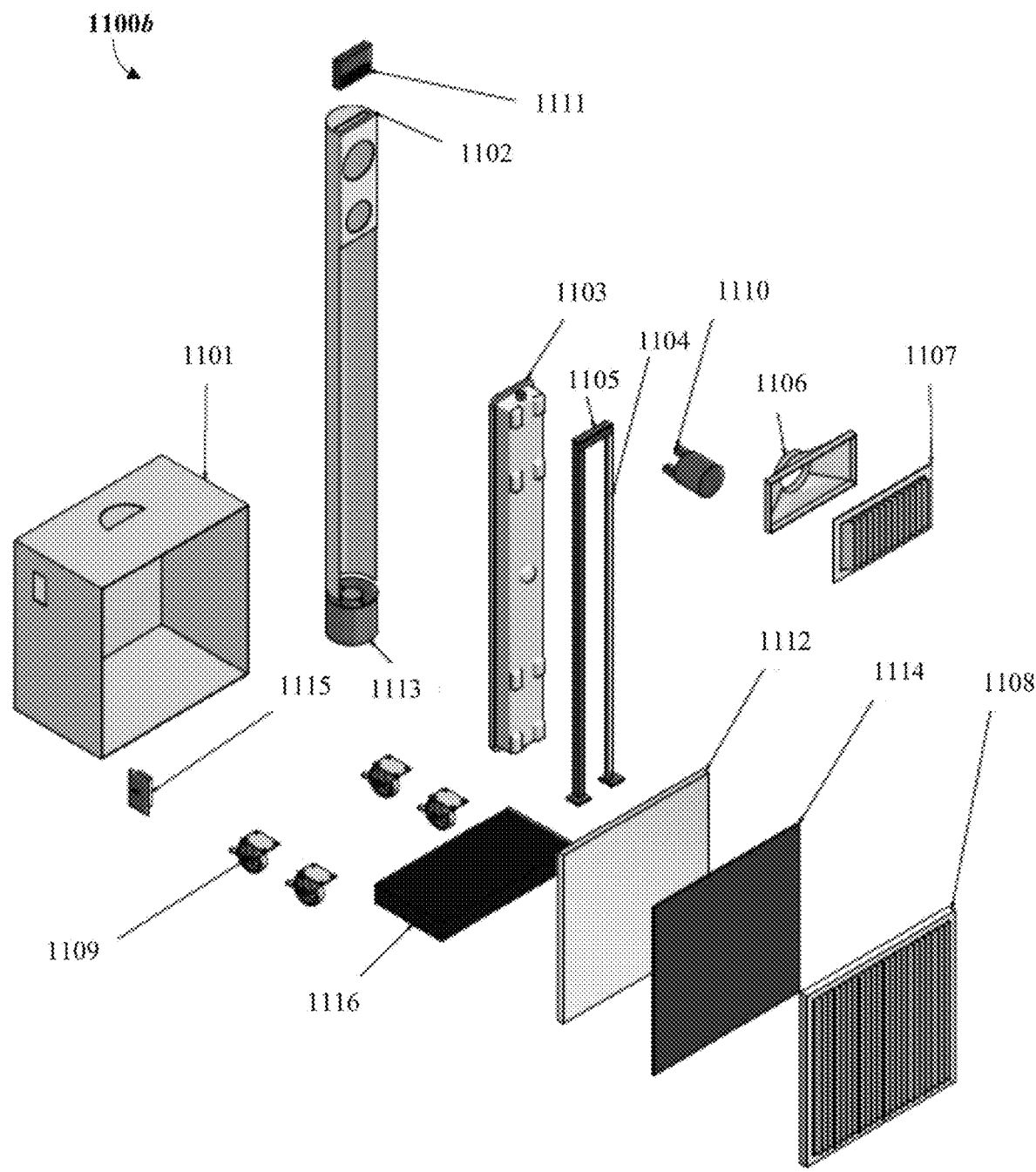
FIG. 11B is an exploded view of a portable airborne pathogen control apparatus, in accordance with certain aspects of the present disclosure.
Figure 12:
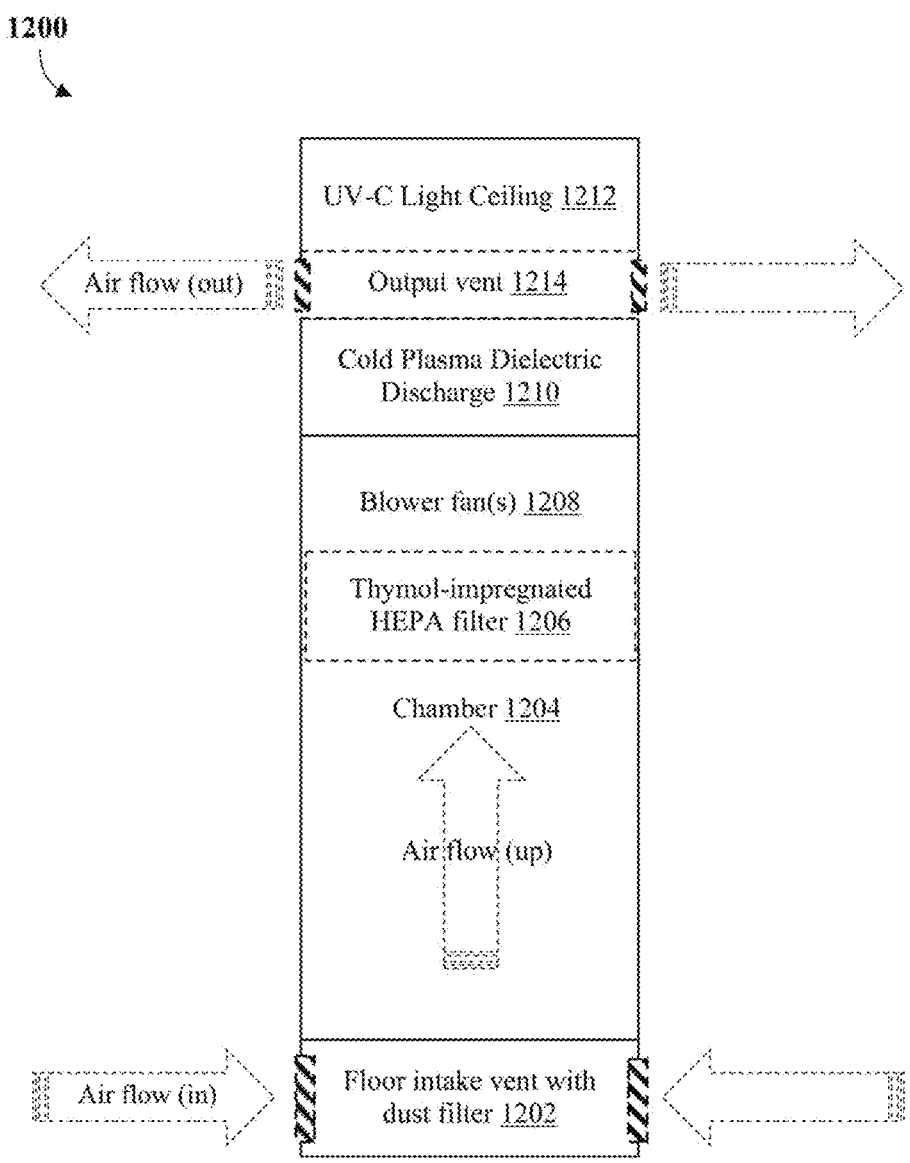
FIG. 12 is a functional block diagram of a portable airborne pathogen control apparatus, in accordance with certain aspects of the present disclosure.
Figure 13:
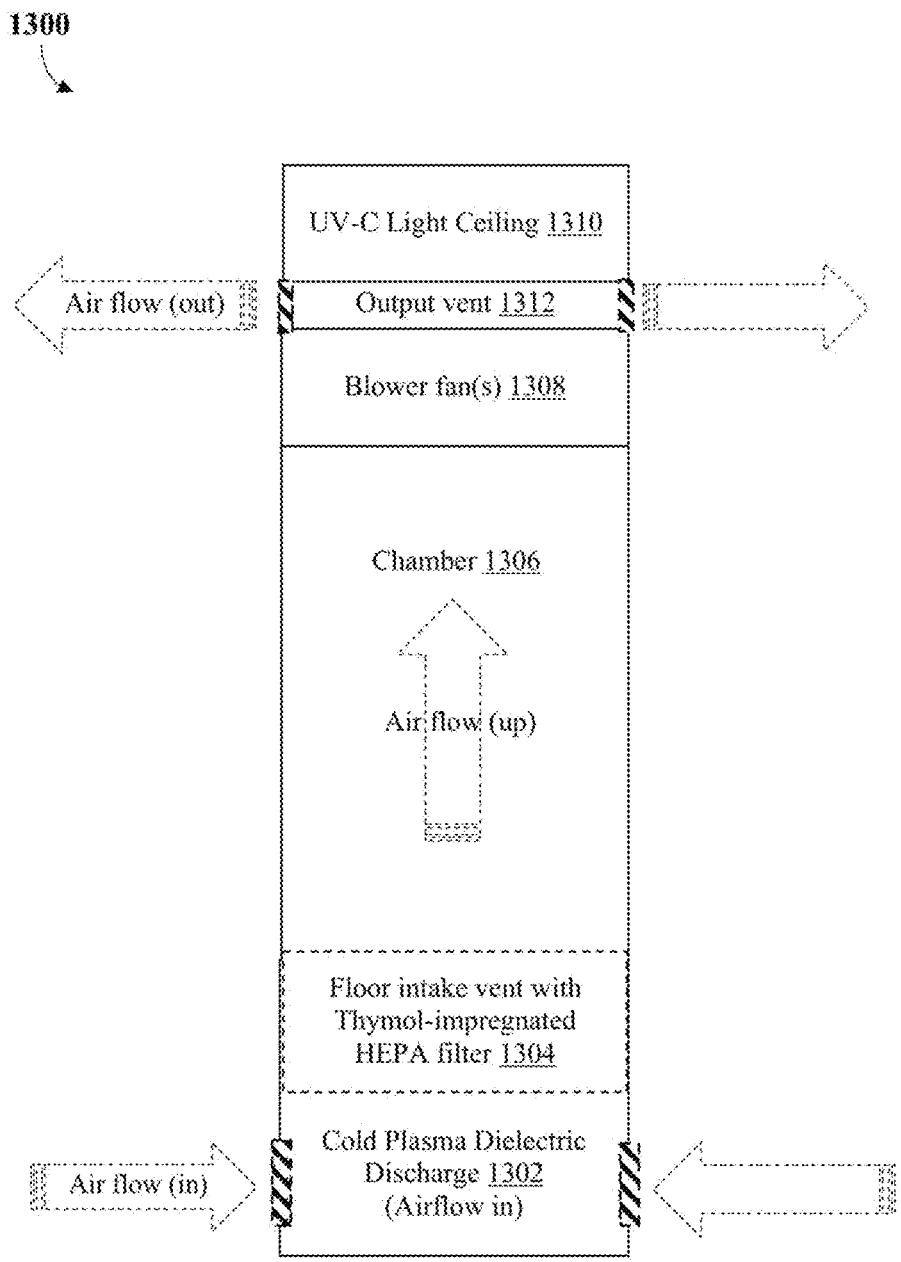
FIG. 13 is a functional block diagram of a portable airborne pathogen control apparatus, in accordance with certain aspects of the present disclosure.

Turning now descriptively to FIGS. 11A and 11B, a portable airborne pathogen control apparatus 1100 is shown. In accordance with certain aspects of the present disclosure, apparatus 1100 may be comprised of a base housing 1101 comprising sidewalls, a bottom and a top defining an interior area. A plurality of wheels 1109 (e.g., four) may be disposed on a lower surface of base housing 1101 to enable apparatus 1100 to be wheeled from one location to another within an interior environment. In certain embodiments, wheels 1109 may comprise four locking caster wheels. In certain embodiments, apparatus 1100 may comprise a counterweight 1116 disposed on a bottom surface of base housing 1101 to prevent apparatus 1100 from tipping or falling during use and/or transport. Apparatus 1100 may further comprise a HEPA filter 1112 disposed on an open area of base housing 1101. In certain embodiments, HEPA filter 1112 may optionally include one or more pre-filter (e.g., dust filter) 1114 disposed on an upstream surface of HEPA filter 1112. Apparatus 1100 may further comprise an air intake vent 1108 disposed on a perimeter of the open area of base housing 1101, adjacent to HEPA filter 1112 (and optional pre-filter 1114).

Still referring to FIGS. 11A and 11B, base housing 1101 may include an airflow aperture or opening disposed on an upper surface of base housing 1101. In accordance with certain aspects of the present disclosure, apparatus 1100 may further comprise an air chamber (e.g., a pipe or other structure) 1102 comprising a lower opening at a first end and an upper opening at a second end. Air chamber 1102 may be coupled to the upper surface of base housing 1101 such that the airflow aperture of base housing 1101 is aligned with the lower opening of air chamber 1102. In certain embodiments, apparatus 1100 may further comprise a blower fan 1113 housed within an interior area of base housing 1101 or air chamber 1102. Blower fan 1113 may be operably configured to selectively establish an airflow (e.g., X cubic feet per minute) from the open area of base housing 1101 to the airflow aperture of base housing 1101 and through the air chamber 1102 from the lower opening to the upper opening.

In accordance with various aspects of the present disclosure, air chamber 1102 is elongated and extends vertically from base housing 1101 such that apparatus 1100 is configured to enable a floor-to-ceiling airflow within an interior room of a building. In accordance with certain aspects of the present disclosure, apparatus 1100 may comprise a UV emitter housing 1103 comprising one or more UV emitters coupled to a surface of air chamber 1102 to establish a closed enclosure with air chamber 1102. In accordance with certain embodiments, the one or more UV emitters may be configured to pulse an emission of radiation at one or more wavelengths in the range of about 200 nm to about 280 nm. In certain embodiments, apparatus 1100 may comprise a frame leg 1104 and a frame plate 1105 configured to removably couple UV emitter housing 1103 to air chamber 1102. In accordance with certain aspects of the present disclosure, apparatus 1100 may comprise a plasma generator 1110 configured to generate a dielectric barrier. In certain embodiments, plasma generator 1110 may be coupled to a surface of air chamber 1102 above UV emitter housing 1103, such that a volume of airflow is exposed to an emission of UV radiation prior to passing over the dielectric barrier generated by plasma generator 1110. In accordance with certain aspects of the present disclosure, apparatus 1100 further comprises an output vent assembly comprising a vent shutter adapter 1106 and an air output vent 1107 coupled to the upper opening of air chamber 1102. In certain embodiments, apparatus 1100 may comprise a particulate counter 1111 comprising at least one optical sensor configured to measure a gross number of particulate present in a volume of air passing through the output vent assembly. In accordance with certain aspects of the present disclosure, apparatus 1100 may comprise a switch 1115 operably configured to control a flow of power from a power source to one or more electronic components of apparatus 1100 (e.g., blower fan 1113, the one or more UV emitters, plasma generator 1110 and particle counter 1111).

Referring now to FIG. 12, a functional block diagram of a portable airborne pathogen control apparatus 1200 is shown. In accordance with certain aspects of the present disclosure, apparatus 1200 may be configured to establish an airflow path from a lower surface of apparatus 1200 at an air intake vent (air flow in), through an interior area of apparatus 1200 to an upper surface of apparatus 1200 at an air output vent 1312 (air flow out). In accordance with certain aspects of the present disclosure, an airflow path is established by apparatus 1200 upon engaging blower fan(s) 1208 to draw a volume of air through floor intake vent with a dust filter 1202 at a lower surface of apparatus 1200. The volume of air is drawn upward through an interior chamber 1204 and is drawn through a Thymol-impregnated HEPA filter 1206. Blower fan(s) 1208 draw the volume of air upward across a cold plasma dielectric discharge 1210. The volume of air is exposed to an emission of UV radiation (e.g., UV-C radiation) from a UV-C light ceiling 1212 before being discharged at an output vent 1214 of apparatus 1200. UV-C light ceiling 1212 may comprise a plurality of a UV-C emitters disposed at an upper interior surface of output vent 1214 and configured to pulse an emission of UV-C radiation to the volume of air passing through output vent 1214 prior to being discharged (air flow out).

Referring now to FIG. 13, a functional block diagram of a portable airborne pathogen control apparatus is shown. In accordance with certain aspects of the present disclosure, apparatus 1300 may be configured to establish an airflow path from a lower surface of apparatus 1300 at an air intake vent (air flow in), through an interior area of apparatus 1300 to an upper surface of apparatus 1300 at an air output vent 1312 (air flow out). In accordance with certain aspects of the present disclosure, an airflow path is established by apparatus 1300 upon engaging blower fan(s) 1308 to draw a volume of air through floor intake vent at a lower surface of apparatus 1300. Blower fan(s) 1308 is further operable to draw the volume of air upward through apparatus 1300 across a cold plasma dielectric barrier 1302 through a Thymol-impregnated HEPA filter 1304 and upward through an interior chamber 1306. The volume of air is exposed to an emission of UV radiation (e.g., UV-C radiation) from a UV-C light ceiling 1310 before being discharged at an output vent 1312 of apparatus 1300. UV-C light ceiling 1310 may comprise a plurality of a UV-C emitters disposed at an upper interior surface of output vent 1312 and configured to pulse an emission of UV-C radiation to the volume of air passing through output vent 1312 prior to being discharged.

In accordance with certain aspects of the present disclosure, the embodiments of the portable airborne pathogen control apparatus described herein may comprise a housing configured to be mounted to a wall of an interior room and comprise an air intake adjacent to a floor of the interior room and an air outlet adjacent to a ceiling of the interior room to enable a floor-to-ceiling airflow within the interior room. In accordance with certain aspects of the present disclosure, the housing of the portable airborne pathogen control apparatus may have a profile depth in the range of about 3 inches to about 12 inches when mounted to the wall of the interior room.

In accordance with certain aspects of the present disclosure, the embodiments of the portable airborne pathogen control apparatus described herein may comprise a housing comprising an "I-shaped" design comprising a baseboard intake vent and a ceiling outflow vent containing a germicidal UV-C light bar in the ceiling outflow vent. In accordance with certain aspects of the present disclosure, the portable airborne pathogen control apparatus may comprise a flexible intake and/or outflow vent configured to direct a flow of air into and/or out of an interior room to create a negative pressure or positive pressure environment within the interior room.

In accordance with certain aspects of the present disclosure, the embodiments of the portable airborne pathogen control apparatus described herein may comprise a housing configured to be removably coupled to a hospital bed and comprising an intake vent at the foot of the bed or under the bed and an output vent at the head of the bed.

The terminology used herein is for describing particular embodiments only and is not intended to be limiting of the embodiments. As used herein, the singular forms "a," "an," and "the" are intended to include the plural forms as well, unless the context clearly indicates otherwise. It will be further understood that the terms "comprises," "comprising," "includes," and/or "including,", and variants thereof, when used herein, specify the presence of stated features, steps, operations, elements, and/or components, but do not preclude the presence or addition of one or more other features, steps, operations, elements, components, and/or groups thereof. As used herein, "exemplary" means serving as an example or illustration and does not necessarily denote ideal or best.

It will be understood that when an element is referred to as being "coupled," "connected," or "responsive" to another element, it can be directly coupled, connected, or responsive to the other element, or intervening elements may also be present. In contrast, when an element is referred to as being "directly coupled," "directly connected," or "directly responsive" to another element, there are no intervening elements present. As used herein, the term "and/or" includes any and all combinations of one or more of the associated listed items.

Spatially relative terms, such as "above," "below," "upper," "lower," "top," "bottom," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly. Well-known functions or constructions may not be described in detail for brevity and/or clarity.

It will be understood that, although the terms "first," "second," etc. may be used herein to describe various elements, these elements should not be limited by these terms. These terms are only used to distinguish one element from another. Thus, a first element could be termed a second element without departing from the teachings of the present embodiments. Unless otherwise defined, all terms (including technical and scientific terms) used herein have the same meaning as commonly understood by one of ordinary skill in the art to which these embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention. Therefore, it will be apparent to those skilled in the art that various modifications and variations can be made to the disclosed embodiments without departing from the scope or spirit of the invention. In view of the foregoing, it is intended that the invention covers modifications and variations of this disclosure within the scope of the following claims and their equivalents.

What is claimed is:

1. A portable airborne pathogen control apparatus comprising:
    a base housing comprising a plurality of wheels coupled to a bottom surface of the base housing;
    an air intake vent disposed on a surface of the base housing;
    a HEPA filter disposed in an interior portion of the base housing;
    an air chamber comprising an elongated duct,
    wherein a first end of the air chamber is coupled to an aperture disposed on an upper surface of the base housing;
    at least one UV-C emitter disposed in an interior portion of the air chamber, wherein the at least one UV-C emitter is configured to pulse an emission of UV radiation to the interior portion of the air chamber;
    a cold plasma generator coupled to a portion of the air chamber;
    an air output vent coupled to an upper portion of the air chamber; and
    a blower fan coupled to a portion of the air chamber, wherein the blower fan is configured to establish an airflow path from the air intake vent through the HEPA filter and through the air chamber to the air output vent,
    wherein the elongated duct comprises a first airflow aperture at the first end of the air chamber and a second airflow aperture at a second end of the air chamber,
    wherein the elongated duct extends vertically from the upper surface of the base housing such that the airflow path is directed vertically from the base housing through the elongated duct,
    wherein the air output vent is interfaced with the second airflow aperture of the elongated duct,
    wherein the air output vent is oriented perpendicularly to the elongated duct such that a flow of air is directed laterally outward from the second end of the air chamber.

2. The apparatus of claim 1 wherein a surface of the HEPA filter comprises at least one antimicrobial agent disposed thereon, wherein the at least one antimicrobial agent is selected from the group consisting of monoterpene phenol, thymol and carvacrol.

3. The apparatus of claim 1 wherein the second airflow aperture of the elongated duct is oriented perpendicularly to the first airflow aperture of the elongated duct.

4. The apparatus of claim 1 wherein the at least one UV-C emitter is configured to pulse the emission of UV radiation at a wavelength in the range of 200 nm to 280 nm.

5. The apparatus of claim 4 wherein the at least one UV-C emitter is configured to pulse a dual band emission of UV radiation at a first wavelength in the range of 200 nm to 280 nm and a second wavelength in the range of 200 nm to 280 nm, wherein the first wavelength is different from the second wavelength.

6. The apparatus of claim 1 further comprising a particulate counter comprising at least one optical sensor configured to measure a gross number of particulate present in a volume of air passing through the air output vent.

7. The apparatus of claim 1 further comprising one or more pre-filter disposed on an upstream surface of the HEPA filter.

8. The apparatus of claim 1 further comprising a counterweight disposed on the bottom surface of the base housing.

9. A portable airborne pathogen control apparatus comprising:
    a housing comprising a bottom, side walls and a top defining an exterior surface and an internal chamber defining an airflow path from an air intake aperture disposed on a lower area of the housing to an air outlet aperture disposed on an upper area of the housing;
    an elongated duct coupled to the upper area of the housing, the elongated duct comprising a first airflow aperture at a first end of the elongated duct and a second airflow aperture at a second end of the elongated duct,
    wherein the first airflow aperture of the elongated duct is interfaced with the air outlet aperture of the housing,
    wherein the elongated duct extends vertically from the upper area of the housing;
    at least one air filter housed in the internal chamber of the housing;
    a blower fan housed in the internal chamber of the housing and operably configured to establish a flow of air through the internal chamber from the air intake aperture to the air outlet aperture;
    at least one UV-C emitter housed in the internal chamber of the housing, wherein the at least one UV-C emitter is configured to pulse an emission of UV radiation at a wavelength in the range of 200 nm to 280 nm to an interior portion of the internal chamber; and
    a cold plasma generator housed in the internal chamber of the housing,
    wherein the first airflow aperture of the elongated duct is oriented perpendicularly to the second airflow aperture of the elongated duct such that the flow of air is directed laterally outward from the second end of the elongated duct.

10. The apparatus of claim 9 wherein the at least one UV-C emitter is configured to pulse a dual band emission of UV radiation at a first wavelength in the range of 200 nm to 280 nm and a second wavelength in the range of 200 nm to 280 nm, wherein the first wavelength is different from the second wavelength.

11. The apparatus of claim 9 wherein the housing is configured to be removably coupled to a surface of a wall of an interior room.

12. The apparatus of claim 9 wherein a surface of the at least one air filter comprises at least one antimicrobial agent disposed thereon, wherein the at least one antimicrobial agent is selected from the group consisting of monoterpene phenol, thymol and carvacrol.

13. The apparatus of claim 9 wherein the at least one UV-C emitter is coupled to an interior surface of the top of the housing adjacent to the air outlet aperture.

14. The apparatus of claim 9 further comprising a particulate counter housed in the internal chamber of the housing and comprising at least one optical sensor configured to measure a gross number of particulate present in a volume of air passing through the air outlet aperture.

15. A portable airborne pathogen control apparatus comprising:
- a base housing comprising a bottom, side walls and a top defining an exterior surface and an internal chamber and at least one air inlet aperture on at least one side of the base housing and an air outlet aperture disposed on the top of the base housing;
- an elongated duct coupled to the air outlet aperture on the top of the base housing at a first end of the elongated duct,
- wherein the elongated duct comprises a first airflow aperture at the first end and a second airflow aperture at a second end of the elongated duct,
- wherein the internal chamber of the base housing and an interior area of the elongated duct comprise an airflow path for the portable airborne pathogen control apparatus;
- at least one air filter disposed in the internal chamber of the base housing;
- a blower fan configured to establish a flow of air through the airflow path from the at least one air inlet aperture to the air outlet aperture;
- at least one UV-C emitter housed in the interior area of the elongated duct; and
- a cold plasma generator housed in the interior area of the elongated duct,
- wherein the elongated duct extends vertically from the top of the base housing such that the airflow path is directed vertically from the base housing through the elongated duct,
- wherein the second airflow aperture is oriented perpendicular to the top of the base housing such that the flow of air is directed laterally outward from the second end of the elongated duct.

16. The apparatus of claim 15 wherein the at least one UV-C emitter is configured to pulse an emission of UV radiation at a wavelength in the range of 200 nm to 280 nm.

17. The apparatus of claim 15 further comprising a particulate counter housed in the interior area of the elongated duct and comprising at least one optical sensor configured to measure a gross number of particulate present in a volume of air passing through the air outlet aperture.

18. The apparatus of claim 15 wherein the blower fan, the base housing and the elongated duct are configured to establish a floor-to-ceiling flow of air in an interior room of a building.

* * * * *